United States Patent
Utsch et al.

(10) Patent No.: US 9,226,808 B2
(45) Date of Patent: *Jan. 5, 2016

(54) ATTACHMENT SECTION FOR AN ORAL HYGIENE DEVICE

(75) Inventors: Joern Utsch, Eschborn (DE); Norbert Schaefer, Frankfurt am Main (DE)

(73) Assignee: BRAUN GMBH, Kronberg (DE)

( * ) Notice: Subject to any disclaimer, the term of this patent is extended or adjusted under 35 U.S.C. 154(b) by 471 days.

This patent is subject to a terminal disclaimer.

(21) Appl. No.: 13/557,240

(22) Filed: Jul. 25, 2012

(65) Prior Publication Data

US 2013/0029289 A1 Jan. 31, 2013

(30) Foreign Application Priority Data

Jul. 25, 2011 (EP) ..................................... 11006065

(51) Int. Cl.
*A61C 17/34* (2006.01)
*A61C 17/22* (2006.01)

(52) U.S. Cl.
CPC .............. *A61C 17/222* (2013.01); *A61C 17/34* (2013.01); *A61C 17/3436* (2013.01)

(58) Field of Classification Search
CPC .............................. A61C 17/222; A61C 17/34
USPC ...................... 15/22.1, 22.2, 23, 28
See application file for complete search history.

(56) References Cited

U.S. PATENT DOCUMENTS

| | | |
|---|---|---|
| 2,798,241 A | 7/1957 | Cohen |
| 3,109,619 A | 11/1963 | Krug et al. |
| 3,220,039 A | 11/1965 | Dayton et al. |
| 3,417,417 A | 12/1968 | Rhodes |
| 3,461,874 A | 8/1969 | Martinez |
| 3,496,500 A | 2/1970 | Romary |
| 3,571,544 A | 3/1971 | Sheehan |
| 3,782,799 A | 1/1974 | Hansen |
| 3,796,850 A | 3/1974 | Moreland, II et al. |
| 3,802,420 A | 4/1974 | Moffat et al. |

(Continued)

FOREIGN PATENT DOCUMENTS

| | | |
|---|---|---|
| AU | 2005100387 A4 | 5/2005 |
| CH | 688 537 A5 | 11/1997 |

(Continued)

OTHER PUBLICATIONS

U.S. Appl. No. 13/557,243, filed Jul. 25, 2012, Utsch et al.

(Continued)

*Primary Examiner* — Randall Chin
(74) *Attorney, Agent, or Firm* — Vladimir Vitenberg

(57) ABSTRACT

An attachment section suitable for connection to a handle section of an oral hygiene device is disclosed. The attachment section includes an attachment housing having a first coupling structure suitable for establishing a connection with a second coupling structure of the handle section; at least a functional element mounted at the attachment housing for driven movement; a motion transmitter extending in a cavity formed inside of the attachment housing, the motion transmitter being functionally connected on one end with the functional element; and a first magnetic coupling element arranged at another end of the motion transmitter, the first magnetic coupling element including at least a permanent magnet or a magnetizable element suitable for establishing a magnetic connection with a second magnetic coupling element provided in the handle section.

7 Claims, 11 Drawing Sheets

(56) References Cited

U.S. PATENT DOCUMENTS

| | | |
|---|---|---|
| 3,810,147 A | 5/1974 | Lichtblau |
| 3,904,841 A | 9/1975 | Swatman |
| 4,156,620 A | 5/1979 | Clemens |
| 4,274,070 A | 6/1981 | Thiene |
| 4,333,197 A | 6/1982 | Kuris |
| 4,349,814 A | 9/1982 | Akehurst |
| 4,352,098 A | 9/1982 | Stephen et al. |
| 4,365,376 A | 12/1982 | Oda et al. |
| 4,371,118 A | 2/1983 | Sontheimer et al. |
| 4,374,354 A | 2/1983 | Petrovic et al. |
| 4,413,199 A | 11/1983 | Fischer |
| 4,420,851 A | 12/1983 | Wiener |
| 4,492,574 A | 1/1985 | Warrin et al. |
| 4,502,497 A | 3/1985 | Siahou |
| 4,506,400 A | 3/1985 | Klein |
| 4,514,172 A | 4/1985 | Behringer |
| 4,523,083 A | 6/1985 | Hamilton |
| 4,546,266 A | 10/1985 | Zenick et al. |
| 4,595,849 A | 6/1986 | Cuenoud |
| 4,595,850 A | 6/1986 | Woog |
| 4,603,448 A | 8/1986 | Middleton et al. |
| 4,682,587 A | 7/1987 | Curlee |
| 4,698,869 A | 10/1987 | Mierau et al. |
| 4,704,602 A | 11/1987 | Asbrink |
| 4,716,614 A | 1/1988 | Jones et al. |
| 4,736,207 A | 4/1988 | Siikaria et al. |
| 4,820,152 A | 4/1989 | Warrin et al. |
| 4,827,550 A | 5/1989 | Graham et al. |
| 4,845,796 A | 7/1989 | Mosley |
| 4,878,679 A | 11/1989 | Plank et al. |
| 4,900,252 A | 2/1990 | Liefke et al. |
| 4,910,634 A | 3/1990 | Pipkorn |
| 4,914,376 A | 4/1990 | Meyer |
| 5,014,794 A | 5/1991 | Hansson |
| 5,065,137 A | 11/1991 | Herman |
| 5,072,164 A | 12/1991 | Prius et al. |
| 5,099,536 A | 3/1992 | Hirabayashi |
| 5,165,131 A | 11/1992 | Staar |
| 5,168,186 A | 12/1992 | Yashiro |
| 5,184,959 A | 2/1993 | Oryhon et al. |
| 5,189,751 A | 3/1993 | Giuliani |
| 5,217,478 A | 6/1993 | Rexroth |
| 5,233,323 A | 8/1993 | Burkett et al. |
| 5,259,083 A | 11/1993 | Stansbury, Jr. |
| 5,263,218 A | 11/1993 | Giuliani et al. |
| 5,269,794 A | 12/1993 | Rexroth |
| 5,274,735 A | 12/1993 | Okada |
| 5,289,604 A | 3/1994 | Kressner |
| 5,305,492 A | 4/1994 | Giuliani et al. |
| 5,309,590 A | 5/1994 | Giuliani et al. |
| 5,337,435 A | 8/1994 | Krasner et al. |
| 5,341,534 A | 8/1994 | Serbinski et al. |
| 5,355,544 A | 10/1994 | Dirksing |
| 5,367,599 A | 11/1994 | Okada |
| 5,378,153 A | 1/1995 | Giuliani et al. |
| 5,381,576 A | 1/1995 | Hwang |
| 5,392,028 A | 2/1995 | Pichl |
| 5,404,608 A | 4/1995 | Hommann |
| 5,448,792 A | 9/1995 | Wiedmann et al. |
| 5,476,384 A | 12/1995 | Giuliani et al. |
| 5,502,861 A | 4/1996 | Spieler et al. |
| 5,504,959 A | 4/1996 | Yukawa et al. |
| 5,524,312 A | 6/1996 | Tan et al. |
| 5,544,382 A | 8/1996 | Giuliani et al. |
| 5,561,881 A | 10/1996 | Klinger et al. |
| 5,576,693 A | 11/1996 | Tyren et al. |
| 5,577,285 A | 11/1996 | Drossler |
| 5,613,259 A | 3/1997 | Craft et al. |
| 5,617,503 A | 4/1997 | Fronen et al. |
| 5,617,601 A | 4/1997 | McDougall |
| 5,673,451 A | 10/1997 | Moore et al. |
| 5,693,042 A | 12/1997 | Boiarski et al. |
| 5,700,146 A | 12/1997 | Kucar |
| 5,732,432 A | 3/1998 | Hui |
| 5,749,885 A | 5/1998 | Sjostrom et al. |
| 5,760,580 A | 6/1998 | Tyren |
| 5,781,955 A | 7/1998 | Hendricks |
| 5,784,742 A | 7/1998 | Giuliani et al. |
| 5,799,356 A | 9/1998 | Kawashima |
| 5,812,065 A | 9/1998 | Schrott et al. |
| 5,815,872 A | 10/1998 | Meginniss, III et al. |
| 5,836,030 A | 11/1998 | Hazeu et al. |
| 5,864,288 A | 1/1999 | Hogan |
| 5,888,031 A | 3/1999 | Buck et al. |
| 5,897,315 A | 4/1999 | Nakayama et al. |
| 5,934,908 A | 8/1999 | Woog et al. |
| 5,939,983 A | 8/1999 | Rudell et al. |
| 5,943,723 A | 8/1999 | Hilfinger et al. |
| 5,955,799 A | 9/1999 | Amaya et al. |
| 5,974,615 A | 11/1999 | Schwarz-Hartmann et al. |
| 5,994,855 A | 11/1999 | Lundell et al. |
| 5,998,965 A | 12/1999 | Carlucci et al. |
| 6,017,354 A | 1/2000 | Culp et al. |
| 6,021,538 A | 2/2000 | Kressner et al. |
| 6,029,303 A | 2/2000 | Dewan |
| 6,043,646 A | 3/2000 | Jansseune |
| 6,098,288 A | 8/2000 | Miyagawa et al. |
| 6,133,701 A | 10/2000 | Gokturk et al. |
| 6,140,723 A | 10/2000 | Matsui et al. |
| 6,140,802 A | 10/2000 | Lundell et al. |
| 6,163,258 A | 12/2000 | Rudell et al. |
| 6,177,870 B1 | 1/2001 | Lian et al. |
| 6,193,510 B1 | 2/2001 | Tsimerman |
| 6,195,828 B1 | 3/2001 | Fritsch |
| 6,202,242 B1 | 3/2001 | Salmon et al. |
| 6,212,052 B1 | 4/2001 | Heuer et al. |
| 6,227,853 B1 | 5/2001 | Hansen et al. |
| 6,234,051 B1 | 5/2001 | Bareggi |
| 6,265,789 B1 | 7/2001 | Honda et al. |
| 6,322,573 B1 | 11/2001 | Muryama |
| 6,326,884 B1 | 12/2001 | Wohlrabe |
| 6,353,956 B1 | 3/2002 | Berge |
| 6,359,559 B1 | 3/2002 | Rudell et al. |
| 6,367,108 B1 | 4/2002 | Fritsch et al. |
| 6,389,633 B1 | 5/2002 | Rosen |
| 6,422,566 B1 | 7/2002 | Rudell et al. |
| 6,441,571 B1 | 8/2002 | Ibuki et al. |
| 6,446,294 B1 | 9/2002 | Specht |
| 6,453,497 B1 | 9/2002 | Chiang et al. |
| 6,498,456 B2 | 12/2002 | Ettes et al. |
| 6,517,348 B1 | 2/2003 | Ram |
| 6,531,873 B1 | 3/2003 | Wohlrabe |
| 6,536,068 B1 | 3/2003 | Yang et al. |
| 6,538,402 B2 | 3/2003 | Gokturk et al. |
| 6,545,576 B1 | 4/2003 | Marchini et al. |
| 6,590,763 B2 | 7/2003 | Kishimoto |
| 6,611,780 B2 | 8/2003 | Lundell et al. |
| 6,623,698 B2 | 9/2003 | Kuo |
| 6,636,135 B1 | 10/2003 | Vetter |
| 6,648,641 B1 | 11/2003 | Viltro et al. |
| 6,716,028 B2 | 4/2004 | Rahman et al. |
| 6,731,213 B1 | 5/2004 | Smith |
| 6,734,795 B2 | 5/2004 | Price |
| 6,735,802 B1 | 5/2004 | Lundell et al. |
| 6,750,747 B2 | 6/2004 | Mandell et al. |
| 6,754,928 B1 | 6/2004 | Rosen |
| 6,760,945 B2 | 7/2004 | Ferber et al. |
| 6,766,824 B2 | 7/2004 | Taylor |
| 6,792,640 B2 | 9/2004 | Levy et al. |
| 6,798,169 B2 | 9/2004 | Stratmann et al. |
| 6,811,399 B2 | 11/2004 | Rahman et al. |
| 6,813,793 B2 | 11/2004 | Eliav |
| 6,845,537 B2 | 1/2005 | Wong |
| 6,850,167 B2 | 2/2005 | Rosen |
| 6,859,968 B2 | 3/2005 | Miller et al. |
| 6,868,919 B1 | 3/2005 | Manschitz et al. |
| 6,873,067 B2 | 3/2005 | Ichii et al. |
| 6,889,401 B2 | 5/2005 | Fattori et al. |
| 6,891,287 B2 | 5/2005 | Moret |
| 6,895,630 B2 | 5/2005 | Tini |
| 6,899,538 B2 | 5/2005 | Matoba |
| 6,918,300 B2 | 7/2005 | Grez et al. |
| 6,952,855 B2 | 10/2005 | Lev et al. |
| 6,954,961 B2 | 10/2005 | Ferber et al. |

(56) References Cited

U.S. PATENT DOCUMENTS

| | | |
|---|---|---|
| 6,958,553 B2 | 10/2005 | Ichii et al. |
| 6,964,076 B2 | 11/2005 | Zhuan |
| 6,966,093 B2 | 11/2005 | Eliav et al. |
| 6,973,694 B2 | 12/2005 | Schutz et al. |
| 7,011,520 B2 | 3/2006 | Rahman et al. |
| 7,024,717 B2 | 4/2006 | Hilscher et al. |
| 7,067,945 B2 | 6/2006 | Grez et al. |
| 7,086,111 B2 | 8/2006 | Hilscher et al. |
| 7,117,555 B2 | 10/2006 | Fattori et al. |
| 7,120,960 B2 | 10/2006 | Hilscher et al. |
| 7,140,058 B2 | 11/2006 | Gatzemeyer et al. |
| 7,174,972 B2 | 2/2007 | Kristen et al. |
| 7,194,862 B2 | 3/2007 | Sattinger |
| 7,207,080 B2 | 4/2007 | Hilscher et al. |
| 7,248,892 B2 | 7/2007 | White et al. |
| 7,258,546 B2 | 8/2007 | Beier et al. |
| 7,258,747 B2 | 8/2007 | Vago et al. |
| 7,288,863 B2 | 10/2007 | Kraus |
| 7,307,397 B2 | 12/2007 | Izumi et al. |
| 7,313,422 B2 | 12/2007 | White et al. |
| 7,315,098 B2 | 1/2008 | Kunita et al. |
| 7,334,283 B2 | 2/2008 | Kunita et al. |
| 7,373,170 B2 | 5/2008 | White et al. |
| 7,376,439 B2 | 5/2008 | White et al. |
| 7,386,904 B2 | 6/2008 | Fattori |
| 7,392,059 B2 | 6/2008 | White et al. |
| 7,409,741 B2 | 8/2008 | Dworzan |
| 7,411,511 B2 | 8/2008 | Kennish et al. |
| 7,422,582 B2 | 9/2008 | Malackowski et al. |
| 7,430,776 B2 | 10/2008 | Eliav |
| 7,431,682 B2 | 10/2008 | Zeiler et al. |
| 7,443,058 B2 | 10/2008 | Shimizu et al. |
| 7,443,059 B2 | 10/2008 | Kobayashi et al. |
| 7,448,108 B2 | 11/2008 | Gatzmeyer et al. |
| 7,469,703 B2 | 12/2008 | France et al. |
| 7,474,018 B2 | 1/2009 | Shimizu et al. |
| 7,474,065 B2 | 1/2009 | Kraus |
| 7,493,669 B2 | 2/2009 | Miller et al. |
| 7,495,358 B2 | 2/2009 | Kobayashi et al. |
| 7,520,016 B2 | 4/2009 | Kressner |
| 7,521,840 B2 | 4/2009 | Heim |
| 7,535,135 B2 | 5/2009 | Kardeis et al. |
| 7,552,497 B2 | 6/2009 | Gatzemeyer et al. |
| 7,562,121 B2 | 7/2009 | Berisford et al. |
| 7,621,015 B2 | 11/2009 | Hilscher et al. |
| 7,624,467 B2 | 12/2009 | Hilscher et al. |
| 7,627,922 B2 | 12/2009 | Miller et al. |
| 7,636,976 B2 | 12/2009 | Banning |
| 7,646,117 B2 | 1/2010 | Shimizu et al. |
| 7,654,271 B2 | 2/2010 | Wyatt et al. |
| 7,661,172 B2 | 2/2010 | Hilscher et al. |
| 7,673,360 B2 | 3/2010 | Hilscher et al. |
| 7,676,875 B2 | 3/2010 | Cho |
| 7,687,944 B2 | 3/2010 | Benning et al. |
| 7,698,771 B2 | 4/2010 | Gall |
| 7,712,174 B2 | 5/2010 | Shimizu et al. |
| 7,750,532 B2 | 7/2010 | Heim |
| 7,770,251 B2 | 8/2010 | Hilscher et al. |
| 7,774,886 B2 | 8/2010 | Hilscher et al. |
| 7,784,136 B2 | 8/2010 | Gatzemeyer et al. |
| 7,784,144 B2 | 8/2010 | Renault |
| 7,810,199 B2 | 10/2010 | Kressner |
| 7,827,644 B2 | 11/2010 | Eliav |
| 7,845,039 B2 | 12/2010 | Chan et al. |
| 7,849,549 B2 | 12/2010 | Hegemann et al. |
| 7,861,348 B2 | 1/2011 | Chan |
| 7,861,349 B2 | 1/2011 | Hilscher et al. |
| 7,876,003 B2 | 1/2011 | Bax |
| 7,877,832 B2 | 2/2011 | Reinbold |
| 7,887,559 B2 | 2/2011 | Deng et al. |
| 7,979,938 B2 | 7/2011 | Lilley et al. |
| 7,979,939 B2 | 7/2011 | Hilscher et al. |
| 8,015,648 B2 | 9/2011 | Hall |
| 8,020,238 B2 | 9/2011 | Eliav et al. |
| 8,021,065 B2 | 9/2011 | Lou |
| 8,032,964 B2 | 10/2011 | Farrell et al. |
| 8,032,965 B2 | 10/2011 | Asada et al. |
| 8,035,487 B2 | 10/2011 | Malackowski |
| 8,060,971 B1 * | 11/2011 | Castelluccio ............. 15/160 |
| 8,089,227 B2 | 1/2012 | Baertschi et al. |
| 8,143,817 B2 | 3/2012 | Izumi et al. |
| 8,181,301 B2 | 5/2012 | Hilscher et al. |
| 8,185,991 B2 | 5/2012 | Kressner |
| 8,218,711 B2 | 7/2012 | Neyer |
| 8,264,105 B2 | 9/2012 | Bax |
| 8,288,970 B2 | 10/2012 | Miller et al. |
| 8,314,586 B2 | 11/2012 | Lumbantobing et al. |
| 8,317,424 B2 | 11/2012 | Chenvainu et al. |
| 8,336,155 B2 | 12/2012 | Crossman et al. |
| 8,341,791 B2 | 1/2013 | Iwahori et al. |
| 2002/0084707 A1 | 7/2002 | Tang |
| 2002/0088068 A1 | 7/2002 | Levy et al. |
| 2002/0127512 A1 | 9/2002 | Chen et al. |
| 2002/0196113 A1 | 12/2002 | Rudd et al. |
| 2003/0017874 A1 | 1/2003 | Jianfei et al. |
| 2003/0093103 A1 | 5/2003 | Malackowski et al. |
| 2003/0097723 A1 | 5/2003 | Li |
| 2003/0115694 A1 | 6/2003 | Pace |
| 2004/0060137 A1 | 4/2004 | Eliav |
| 2004/0068811 A1 | 4/2004 | Fulop et al. |
| 2004/0123409 A1 | 7/2004 | Dickie |
| 2004/0128778 A1 | 7/2004 | Wong |
| 2004/0191724 A1 | 9/2004 | Rahman et al. |
| 2004/0255409 A1 | 12/2004 | Hilscher et al. |
| 2005/0011022 A1 | 1/2005 | Kwong |
| 2005/0011023 A1 | 1/2005 | Chan |
| 2005/0037316 A1 | 2/2005 | Sholder |
| 2005/0102776 A1 | 5/2005 | Mathur |
| 2005/0128051 A1 | 6/2005 | Dickinson et al. |
| 2005/0235438 A1 | 10/2005 | Motohashi et al. |
| 2005/0271531 A1 | 12/2005 | Brown, Jr. et al. |
| 2005/0272001 A1 | 12/2005 | Blain et al. |
| 2005/0278877 A1 | 12/2005 | Akridge et al. |
| 2006/0027246 A1 | 2/2006 | Wilkinson |
| 2006/0032006 A1 | 2/2006 | Brown et al. |
| 2006/0048315 A1 | 3/2006 | Chan et al. |
| 2006/0048797 A1 | 3/2006 | Jung et al. |
| 2006/0145871 A1 | 7/2006 | Donati et al. |
| 2007/0000079 A1 | 1/2007 | Mori et al. |
| 2007/0130705 A1 | 6/2007 | Chan et al. |
| 2007/0234493 A1 | 10/2007 | Hilscher et al. |
| 2008/0020351 A1 | 1/2008 | Hilscher et al. |
| 2008/0022470 A1 | 1/2008 | Hilscher et al. |
| 2008/0022501 A1 | 1/2008 | Hilscher et al. |
| 2008/0022503 A1 | 1/2008 | Hilscher et al. |
| 2008/0028549 A1 | 2/2008 | Hilscher et al. |
| 2008/0032265 A1 | 2/2008 | Hilscher et al. |
| 2008/0034515 A1 | 2/2008 | Hilscher et al. |
| 2008/0083075 A1 | 4/2008 | Dickie |
| 2008/0102419 A1 | 5/2008 | Sauter et al. |
| 2008/0196735 A1 | 8/2008 | Wyatt et al. |
| 2008/0254407 A1 | 10/2008 | Benning et al. |
| 2008/0293009 A1 | 11/2008 | Winston |
| 2009/0177125 A1 | 7/2009 | Pilcher et al. |
| 2009/0183324 A1 | 7/2009 | Fischer et al. |
| 2009/0211043 A1 | 8/2009 | Kressner |
| 2009/0241276 A1 | 10/2009 | Hall et al. |
| 2009/0243520 A1 | 10/2009 | Kashiwabara et al. |
| 2009/0320221 A1 | 12/2009 | Masuko |
| 2010/0132139 A1 | 6/2010 | Jungnickel |
| 2010/0154151 A1 * | 6/2010 | Grez et al. ............. 15/22.1 |
| 2010/0301620 A1 | 12/2010 | Luckel et al. |
| 2010/0306934 A1 | 12/2010 | Headstrom |
| 2011/0005015 A1 | 1/2011 | Iwahori et al. |
| 2011/0041268 A1 | 2/2011 | Iwahori et al. |
| 2011/0080122 A1 | 4/2011 | Klemm et al. |
| 2011/0107531 A1 | 5/2011 | Ye |
| 2011/0138551 A1 | 6/2011 | Stopler et al. |
| 2011/0181208 A1 | 7/2011 | Murata |
| 2011/0181209 A1 | 7/2011 | Murata |
| 2011/0181211 A1 | 7/2011 | Murata |
| 2011/0203061 A1 | 8/2011 | Takahashi et al. |
| 2011/0248085 A1 | 10/2011 | Hilscher et al. |
| 2011/0252584 A1 | 10/2011 | Jousma et al. |

(56) References Cited

U.S. PATENT DOCUMENTS

| | | |
|---|---|---|
| 2011/0258793 A1 | 10/2011 | Jousma et al. |
| 2011/0273153 A1 | 11/2011 | Lepper et al. |
| 2012/0036665 A1 | 2/2012 | Cho |
| 2012/0042742 A1 | 2/2012 | Utsch et al. |
| 2012/0066848 A1 | 3/2012 | Klemm et al. |
| 2012/0151698 A1 | 6/2012 | Schaefer et al. |
| 2012/0198635 A1 | 8/2012 | Hilscher et al. |
| 2013/0025079 A1 | 1/2013 | Jungnickel et al. |
| 2013/0029289 A1 | 1/2013 | Utsch et al. |

FOREIGN PATENT DOCUMENTS

| | | |
|---|---|---|
| CN | 2048697 | 12/1989 |
| CN | 2124686 | 12/1992 |
| CN | 2149877 | 12/1993 |
| CN | 1098888 A | 2/1995 |
| CN | 2332378 | 8/1999 |
| CN | 1520788 A | 1/2004 |
| CN | 1778278 A | 11/2004 |
| CN | 1778279 A | 11/2004 |
| CN | 1843305 A | 4/2005 |
| CN | 1846651 A | 4/2005 |
| CN | 183043 A | 9/2006 |
| CN | 200980058 | 11/2007 |
| CN | 201055092 Y | 5/2008 |
| CN | 201403746 Y | 10/2008 |
| CN | 201295301 Y | 12/2008 |
| CN | 201187899 Y | 1/2009 |
| CN | 101427944 A | 5/2009 |
| CN | 201341578 Y | 11/2009 |
| CN | 20151881 U | 7/2010 |
| DE | 2413524 | 10/1975 |
| DE | 2826008 C2 | 6/1983 |
| DE | 3708801 A1 | 9/1988 |
| DE | 4036373 C2 | 11/1990 |
| DE | 3936714 | 5/1991 |
| DE | 3937852 | 5/1991 |
| DE | 4012413 | 10/1991 |
| DE | 4036479 | 5/1992 |
| DE | 42 01 027 A1 | 7/1992 |
| DE | 3880015 | 9/1993 |
| DE | 4422086 C1 | 6/1994 |
| DE | 4305013 | 8/1994 |
| DE | 19506129 | 2/1995 |
| DE | 19518935 | 5/1995 |
| DE | 94 11 158 U1 | 8/1995 |
| DE | 29608164 | 5/1996 |
| DE | 19627752 A1 | 7/1996 |
| DE | 19628574 | 3/1997 |
| DE | 19545324 | 6/1997 |
| DE | 1196 03 851 A1 | 8/1997 |
| DE | 29608167 | 9/1997 |
| DE | 29709865 U1 | 10/1997 |
| DE | 198 03 311 A1 | 8/1999 |
| DE | 29915858 U1 | 9/1999 |
| DE | 198 40 684 A1 | 3/2000 |
| DE | 19832607 | 5/2000 |
| DE | 199 13 945 A1 | 9/2000 |
| DE | 19921677 | 11/2000 |
| DE | 19923104 A1 | 11/2000 |
| DE | 10001502 | 3/2001 |
| DE | 10026513 | 5/2001 |
| DE | 201 12 320 U1 | 10/2001 |
| DE | 19953651 | 10/2001 |
| DE | 10135257 | 2/2002 |
| DE | 10045353 | 3/2002 |
| DE | 10045067 | 4/2002 |
| DE | 10101163 | 7/2002 |
| DE | 4243219 A1 | 12/2002 |
| DE | 10153863 | 5/2003 |
| DE | 10154946 | 5/2003 |
| DE | 102 47 698 | 4/2004 |
| DE | 10 2004 029 684 A1 | 12/2005 |
| DE | 10 2005 045 800 A1 | 4/2007 |
| DE | 197 27 018 B4 | 4/2007 |
| EP | 024992 | 6/1984 |
| EP | 046169 | 8/1984 |
| EP | 0085795 | 3/1987 |
| EP | 285915 | 12/1988 |
| EP | 0300345 | 1/1989 |
| EP | 0435329 | 7/1991 |
| EP | 440051 | 8/1991 |
| EP | 391967 B1 | 8/1992 |
| EP | 294548 B1 | 4/1993 |
| EP | 624079 | 10/1993 |
| EP | 634151 | 3/1994 |
| EP | 787469 A1 | 8/1997 |
| EP | 848921 | 6/1998 |
| EP | 1 231 706 A2 | 8/2002 |
| EP | 1267664 | 6/2004 |
| EP | 1379149 | 8/2004 |
| EP | 1244373 | 7/2006 |
| EP | 1 696 539 A1 | 8/2006 |
| EP | 1 737 110 A1 | 12/2006 |
| EP | 1 733 700 B1 | 8/2010 |
| EP | 2 262 083 A1 | 12/2010 |
| FR | 2832298 | 5/2003 |
| GB | 1167444 | 10/1969 |
| GB | 1246564 | 9/1974 |
| GB | 2082713 | 3/1982 |
| GB | 2117230 | 10/1983 |
| GB | 2146893 | 5/1985 |
| GB | 2376758 | 12/2002 |
| GB | 2 412 014 A | 9/2005 |
| JP | 1989083268 | 3/1989 |
| JP | 04-087127 | 3/1992 |
| JP | 04-269906 | 9/1992 |
| JP | 05-269024 | 10/1993 |
| JP | 06-01413 | 1/1994 |
| JP | 07-123600 | 5/1995 |
| JP | 07-177932 | 7/1995 |
| JP | 07-194862 | 8/1995 |
| JP | 08-000358 | 1/1996 |
| JP | 08-066325 | 3/1996 |
| JP | 08-117030 | 5/1996 |
| JP | 1996187125 | 7/1996 |
| JP | 08-275961 | 10/1996 |
| JP | 09-252843 | 9/1997 |
| JP | 1998005041 | 1/1998 |
| JP | 10-127346 | 5/1998 |
| JP | 10-243688 | 9/1998 |
| JP | 28-62873 | 3/1999 |
| JP | 199113638 | 4/1999 |
| JP | 11-318951 | 11/1999 |
| JP | 2000-253639 A | 9/2000 |
| JP | 2001-37788 | 2/2001 |
| JP | 2001-197676 | 7/2001 |
| JP | 2001/346816 | 12/2001 |
| JP | 2001-346816 | 12/2001 |
| JP | 2002/045379 | 2/2002 |
| JP | 2002/306867 | 10/2002 |
| JP | 2002/320399 | 10/2002 |
| JP | 2003/250233 | 9/2003 |
| JP | 2003/348888 | 12/2003 |
| JP | 2004/007890 | 1/2004 |
| JP | 2006-280830 | 10/2006 |
| JP | 2007-000693 | 1/2007 |
| JP | 1998137040 | 5/2008 |
| JP | 2009-100523 | 5/2009 |
| JP | 2010-035315 | 2/2010 |
| JP | 2010-125263 | 6/2010 |
| KR | 2003-0091408 | 12/2003 |
| KR | 10-2005-0043071 | 5/2005 |
| KR | 10-2007-0034649 | 3/2007 |
| KR | 10-0752601 | 8/2007 |
| KR | 10-2007-0107198 | 11/2007 |
| KR | 20-2008-0004243 | 10/2008 |
| KR | 10-2009-106306 | 10/2009 |
| NL | C 1030139 | 10/2005 |
| RU | 2 077 349 C1 | 7/1993 |
| RU | 2 129 826 C1 | 5/1999 |
| SE | 531 401 C2 | 3/2009 |
| SU | 749380 | 7/1980 |

(56) References Cited

FOREIGN PATENT DOCUMENTS

| | | |
|---|---|---|
| SU | 1542539 | 2/1990 |
| WO | WO 91/06258 | 5/1991 |
| WO | WO 95/33419 | 12/1995 |
| WO | WO 97/24079 | 10/1997 |
| WO | WO 98/24527 | 6/1998 |
| WO | WO-98/36703 A1 | 8/1998 |
| WO | WO 98/55274 | 10/1998 |
| WO | WO 99/20202 | 4/1999 |
| WO | WO 99/53562 | 10/1999 |
| WO | WO 00/39768 | 7/2000 |
| WO | WO 00/42584 | 7/2000 |
| WO | WO 00/47128 | 8/2000 |
| WO | WO 00/74591 | 12/2000 |
| WO | WO 01/08591 | 2/2001 |
| WO | WO 01/32052 | 5/2001 |
| WO | WO 01/47392 | 7/2001 |
| WO | WO 01/91603 | 12/2001 |
| WO | WO 02/093881 | 1/2002 |
| WO | WO 02/071972 A1 | 9/2002 |
| WO | WO 02/083257 | 10/2002 |
| WO | WO 02/098315 | 12/2002 |
| WO | WO 03/054771 | 7/2003 |
| WO | WO 2005/096882 A1 | 10/2005 |
| WO | WO 2008/015616 A2 | 2/2008 |
| WO | WO 2008/019864 A2 | 2/2008 |
| WO | WO 2008/098107 A2 | 8/2008 |
| WO | WO 2010/106522 A1 | 9/2010 |
| WO | WO 2010/106850 A1 | 9/2010 |
| WO | WO 2010/143156 A1 | 12/2010 |
| WO | WO 2011/044858 A1 | 4/2011 |
| WO | WO 2011/077289 A1 | 6/2011 |
| WO | WO 2011/077290 A1 | 6/2011 |

OTHER PUBLICATIONS

U.S. Appl. No. 13/213,865, filed Aug. 19, 2011, Klemm et al.
U.S. Appl. No. 13/190,284, filed Jul. 25, 2011, Utsch et al.
U.S. Appl. No. 13/557,245, filed Jul. 25, 2011, Jungnickel et al.
U.S. Appl. No. 13/190,293, filed Jul. 25, 2011, Ziegler et al.
U.S. Appl. No. 13/450,657, filed Apr. 19, 2012, Hilscher et al.
U.S. Appl. No. 13/166,894, filed Jun. 23, 2011, Hilscher et al.
U.S. Appl. No. 12/627,367, filed Nov. 30, 2009, Hilscher et al.
U.S. Appl. No. 11/888,152, filed Jul. 31, 2007, Hilscher et al.
Office Action from U.S. Appl. No. 10/872,075, dated Mar. 24, 2006.
Office Action from U.S. Appl. No. 10/872,075, dated May 15, 2007.
Office Action from U.S. Appl. No. 10/872,075, dated Jun. 4, 2009.
Office Action from U.S. Appl. No. 10/872,075, dated Aug. 1, 2006.
Office Action from U.S. Appl. No. 10/872,075, dated Oct. 31, 2007.
Office Action from U.S. Appl. No. 10/872,075, dated Dec. 10, 2008.
Office Action from U.S. Appl. No. 10/872,075, dated Dec. 27, 2006.
Office Action from U.S. Appl. No. 11/888,386, dated Dec. 3, 2009.
Office Action from U.S. Appl. No. 09/811,080, dated Feb. 3, 2004.
Office Action from U.S. Appl. No. 09/811,080, dated Oct. 1, 2004.
Office Action from U.S. Appl. No. 10/241,274, dated Jan. 14, 2005.
Office Action from U.S. Appl. No. 10/241,274, dated Sep. 1, 2006.
Office Action from U.S. Appl. No. 10/662,237, dated Feb. 18, 2005.
Office Action from U.S. Appl. No. 10/871,469, dated Jan. 9, 2007.
Office Action from U.S. Appl. No. 10/871,469, dated Jul. 25, 2006.
Office Action from U.S. Appl. No. 10/871,469, dated Aug. 24, 2005.
Office Action from U.S. Appl. No. 10/871,469, dated Dec. 27, 2007.
Office Action from U.S. Appl. No. 10/872,016, dated Feb. 7, 2006.
Office Action from U.S. Appl. No. 10/872,016, dated 02/23/20079.
Office Action from U.S. Appl. No. 10/872,016, dated Mar. 7, 2008.
Office Action from U.S. Appl. No. 10/872,016, dated Apr. 10, 2009.
Office Action from U.S. Appl. No. 10/872,016, dated Jun. 24, 2005.
Office Action from U.S. Appl. No. 10/872,016, dated Jul. 10, 2006.
Office Action from U.S. Appl. No. 10/872,016, dated Sep. 20, 2006.
Office Action from U.S. Appl. No. 10/872,016, dated Nov. 9, 2009.
Office Action from U.S. Appl. No. 11/257,603, dated Jan. 18, 2007.
Office Action from U.S. Appl. No. 11/257,603, dated Mar. 21, 2008.
Office Action from U.S. Appl. No. 11/257,603, dated May 15, 2007.
Office Action from U.S. Appl. No. 11/257,603, dated Aug. 30, 2007.
Office Action from U.S. Appl. No. 11/257,603, dated Sep. 20, 2006.
Office Action from U.S. Appl. No. 11/257,603, dated Nov. 25, 2008.
Office Action from U.S. Appl. No. 11/763,338, dated Mar. 24, 2009.
Office Action from U.S. Appl. No. 11/763,338, dated Jul. 10, 2008.
Office Action from U.S. Appl. No. 11/763,338, dated Dec. 4, 2008.
Office Action from U.S. Appl. No. 11/888,212, dated Mar. 17, 2009.
Office Action from U.S. Appl. No. 11/888,212, dated Mar. 21, 2008.
Office Action from U.S. Appl. No. 11/888,250, dated Jun. 30, 2008.
Office Action from U.S. Appl. No. 11/888,251, dated Mar. 17, 2009.
Office Action from U.S. Appl. No. 11/888,251, dated Mar. 21, 2008.
Office Action from U.S. Appl. No. 11/888,386, dated Mar. 3, 2009.
Office Action from U.S. Appl. No. 11/890,083, dated Mar. 16, 2009.
PCT Search Report for PCT/EP 01/02844, dated Aug. 8, 2001.
PCT Search Report for PCT/EP 01/02862, dated Jul. 31, 2001.
PCT Search Report for PCT/EP 02/01724, dated Jul. 17, 2002 for U.S. Appl. No. 10/241,274.
Finkenzeller, Laus, "RFID-Handbuch, Grundlagen und praktische Anwendungen induktiver Funkanlagen, Transponder und kontaktloser Chipkarten" [Trans: "RFID Handbook. Fundamentals and Practical Applications to Inductive Radio Communications, Transponders and Contactless Chip Cards"], Carl Hanser Verlag Munchen, $2^{nd}$ Edtiion, Chapter 3, pp. 29-58 w/title page and Impressum. Contents pp. vii-xviii, and Appendices 15.2 "Standards" and 15.3 "Literature" on pp. 393-406.
Herzer, Gieselher, "Der grosse Lauschangriff auf Ladendiebe" [transl. "The great surveillance of shoplifters"] in Physikalische Blaetter [transl: Physics Letters] vol. 57, (2001), No. 5, pp. 43-48.
Package rear and bottom panels of Bausch & Lomb Interplak Model PB-4B, marked © 1990 (color copy, 1 sheet).
Color photographs of Bausch & Lomb "Interplak" Model PB-6 style Handpiece with waterproof electronic travel protection switch (believed circa 1992 on sale in the United States) (6 views).
Package rear and bottom panels of Bausch & Lomb Interplak Model PB-6, marked © 1992 (color copy, 1 sheet).
Product use instructions to Bausch & Lomb Interplak travel-style "Voyager" model TK-2 marked © 1991 (6 photocopies sheets containing cover and pp. 1-10).
"RFID Made Easy" Handbook by EM Microelectronic-Marin SA, 2074 Marin, Switzerland, copr 2000 and dated Mar. 2001, Rev. C/350, pp. 1-33.
Use instructions to Braun D5 electric toothbrush Type 4726 on sale in US, circa 1991, including description of "Travel lock" switch.
Color photographs of Bausch & Lomb "Interplak" Model PB-4B style Handpiece with travel protection switch and Toothbrush attachment (handpiece stamped "1D IA", believed circa 1992 on sale in the United States) (2 sheets with 7 views).
PCT International Search Report dated Nov. 2, 2011.
European Search Report for EP 11 00 6065 dated Feb. 27, 2012.
Pct Search Report for PCT/IB2012/053780 dated Jun. 21, 2012.
PCT International search Report dated Oct. 28, 2011.
PCT International Search Report for PCT/IB2011/053665 dated Nov. 23, 2012.
PCT International Search Report for PCT/IB2012/053804—dated Nov. 29, 2012.

* cited by examiner

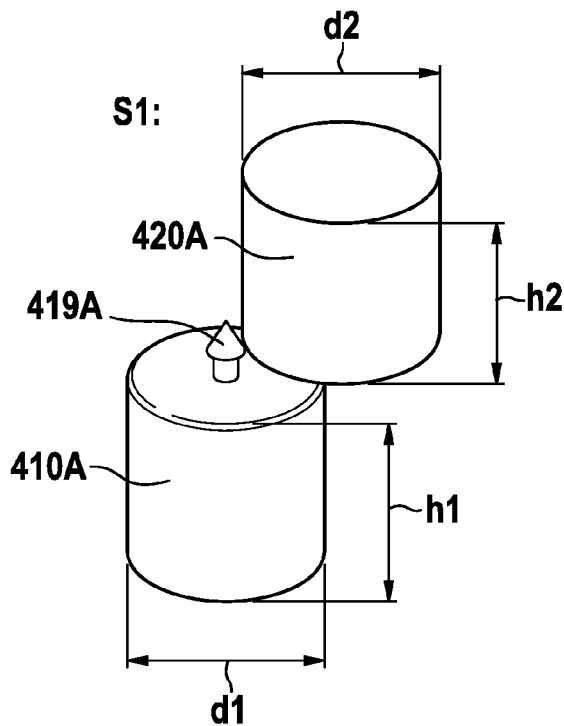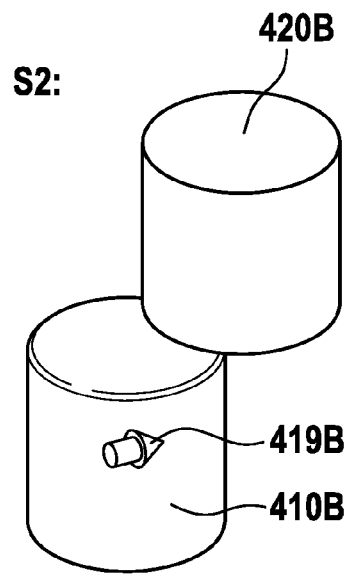
Fig. 6A    Fig. 6B
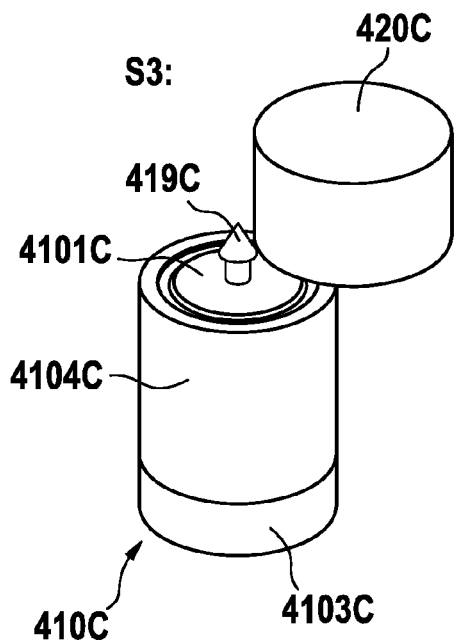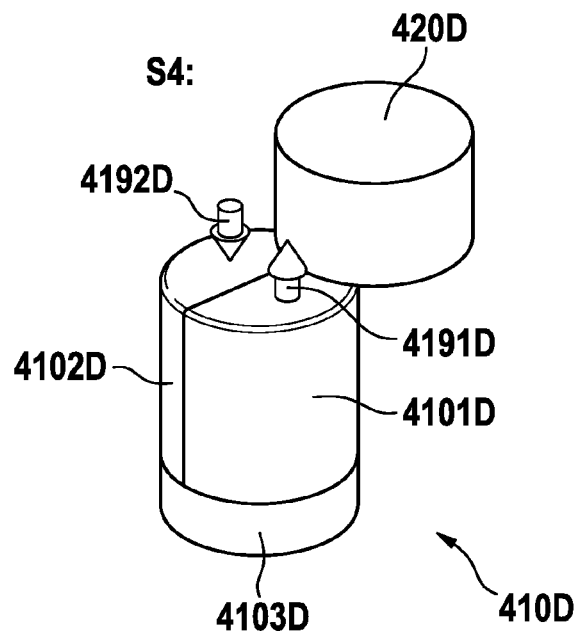
Fig. 6C    Fig. 6D

ATTACHMENT SECTION FOR AN ORAL HYGIENE DEVICE

CROSS REFERENCE TO RELATED APPLICATIONS

This application claims the benefit of European Patent Convention Application No. 11006065.4, filed Jul. 25, 2011, the substance of which is incorporated by reference in its entirety herein.

FIELD OF THE INVENTION

The present disclosure is directed to an attachment section for an oral hygiene device, a handle section for an oral hygiene device and an oral hygiene device.

BACKGROUND OF THE INVENTION

It is known that electric oral hygiene devices, in particular electric toothbrushes, may have detachably mounted replacement attachments such as a replacement brush head of an electric toothbrush. It is further known that the coupling between the attachment and a handle of the oral hygiene device may be realized by mechanical means such as a snap hook provided at the attachment that snaps into a groove provided at the handle. Mechanical couplings often have a certain clearing or gap between the coupling partners due to tolerances between the coupling partners. Such clearings or gaps have the tendency to generate unwanted rattling noise during operation of the device.

There, however, exists a need to provide an improved coupling between an attachment section and a handle section of an oral hygiene device and in particular an attachment section and a handle section that enable such improved coupling.

SUMMARY OF THE INVENTION

In one embodiment, an attachment section suitable for connection to a handle section of an oral hygiene device is provided. The attachment section includes an attachment housing having a first coupling structure suitable for establishing a connection with a second coupling structure of the handle section; at least a functional element mounted at the attachment housing for driven movement; a motion transmitter extending in a cavity formed inside of the attachment housing, the motion transmitter being functionally connected on one end with the functional element; and a first magnetic coupling element arranged at another end of the motion transmitter, the first magnetic coupling element including at least a permanent magnet or a magnetizable element suitable for establishing a magnetic connection with a second magnetic coupling element provided in the handle section.

In another embodiment, a handle section of an oral hygiene device for connection with an attachment section is provided. The handle section includes a second magnetic coupling element arranged at a drive shaft for establishing a magnetic connection with a first magnetic coupling element provided in the attachment section in an attached state; and a second coupling structure for establishing a further connection with a first coupling structure provided at the attachment section. The second magnetic coupling element comprises a permanent magnet that fits into a cylinder having a diameter of at least about 4.5 mm and a length of about at least 4.5 mm.

In yet another embodiment, an attachment section suitable for connection to a handle section of an oral hygiene device is provided. The attachment section includes an attachment housing having a first coupling structure suitable for establishing a connection with a second coupling structure of the handle section; a motion transmitter extending in a cavity formed inside of the attachment housing, the motion transmitter being non-detachably connected at one end with the attachment section; and a first magnetic coupling element being arranged at another end of the motion transmitter, the first magnetic coupling element comprising at least a permanent magnet or a magnetizable element suitable for establishing a magnetic connection with a second magnetic coupling element provided in the handle section. The first magnetic coupling element is retracted from an end of the attachment housing intended for coupling with the handle section by a distance of at least about 5.0 mm.

Further, in some embodiments, there is provided an electric oral hygiene device that comprises at least an attachment section as proposed and a handle section.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

FIGS. 6A-6D show four example configurations of first and second magnetic coupling elements;

DETAILED DESCRIPTION OF THE INVENTION

Figure 1:
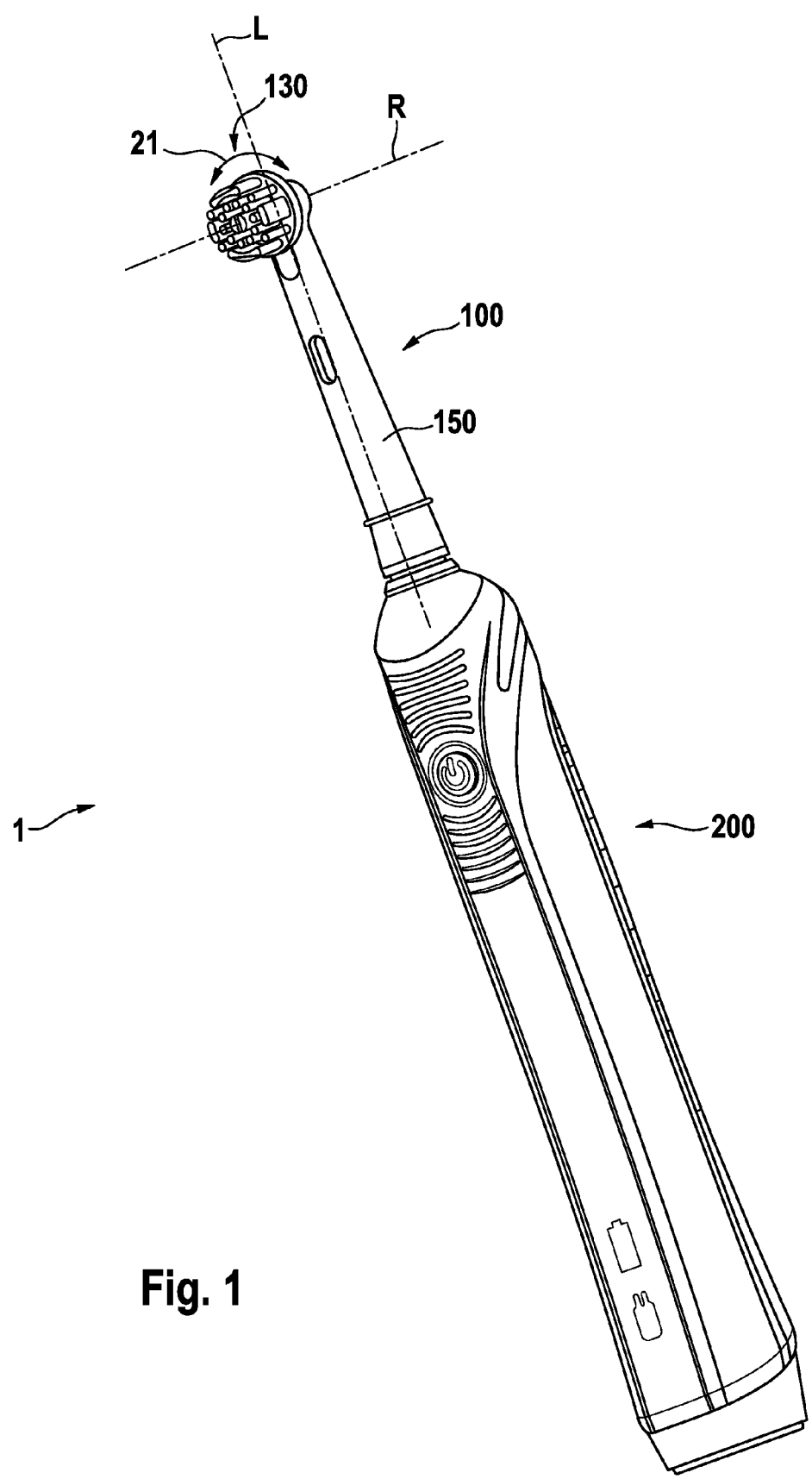
FIG. 1 is a perspective view onto an oral hygiene device in the form of an electric toothbrush.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

One aspect of the present disclosure is concerned with a connection, for example, a detachable connection, between an attachment section and a handle section of an oral hygiene device, for example, an electric toothbrush, where at least one connection (for example, a connection established between movably mounted parts that are driven during operation and are intended for transferring motion from a motor in the handle section to a functional element in the attachment section) between the attachment section and the handle section may be a magnetic coupling. Mechanical couplings in general have inherently tolerance-based clearances or gaps between the coupling partners so that the coupling partners may move relatively to each other when the respective connection is established between parts being driven during operation. Such a mechanical connection is then prone to generate unwanted noise during operation. A magnetic coupling can inherently be designed with less clearance so that a magnetic coupling is likely to produce less noise.

In some embodiments, an attachment section as proposed comprises a first magnetic coupling element that has at least a permanent magnet or a magnetizable element. The first magnetic coupling is arranged for establishing a magnetic connection with a second magnetic coupling element provided in a handle section in an attached state.

In some embodiments, an attachment section may additionally comprise an attachment housing, a functional element mounted for driven motion at the attachment housing and a motion transmitter. The motion transmitter may on one end be coupled to the functional element to transfer motion to the functional element and on another end may be equipped with the first magnetic coupling element. The motion transmitter may in particular extend in a cavity formed inside of the attachment housing. In some embodiments, the functional element may be a working element such as a brush head for cleaning teeth. In some embodiments, the attachment housing may have a first coupling structure intended for establishing a further connection with a second coupling structure provided at the handle section.

In one example, a magnetizable element (e.g. a magnetizable steel or iron element) may be inexpensive to produce, and an attachment section intended for disposal after some period of use may then less expensive for consumers. This is in particular interesting in cases where the costs of a permanent magnet would be in the same order as the costs of the whole attachment section. On the other hand, a permanent magnet in the attachment section together with a permanent magnet in the handle section can provide for a higher coupling strength then a permanent magnet and magnetizable element combination at the same construction volume.

In some embodiments, the first magnetic coupling element comprises a protective cover that protects the first magnetic coupling element from corrosion or abrasion. In such embodiments, the protective cover may be abrasion resistant to the extent that during a typical lifetime of the attachment section the protective cover stays intact. As an oral hygiene device is used in a wet environment and typically with abrasive and/or corrosive chemicals such as mouth rinses or toothpaste, a thin coating such as, for example, a 10 micrometer thick gold coating may be abraded within a rather short period. A protective cover made of an about 20 µm thick or more, optionally about 30 µm or more, further optionally about 40 µm or more, even further optionally about 50 µm or more metal layer, ceramic layer, glass layer or abrasion-resistant plastic or resin layer can be used. In some embodiments, the protective cover may have a thickness of about 60 µm or more, about 70 µm or more, about 80 µm or more, about 90 µm or more, about 100 µm or more, about 150 µm or more or about 200 µm or more, and/or any thickness within or including the values provided above or any ranges including or within the values provided above. In some embodiments, the protective cover may be an essentially cup-shaped element that may be mounted by gluing, press-fitting, crimping, shrink-fitting, stamping, welding, snapping or any combination thereof. The protective cover is, in some particular embodiment, a plate or disk that may be glued to the magnetic coupling element. In some embodiments, a protective cover is used that is manufactured in a deep-drawing, punch-drawing or thermoforming process.

In general, the protective cover may be designed to be abrasion resistant for a temporary period which corresponds to a typical period of use of the attachment section. The typical period of use may be about three months with three a switch-on periods of two to four minutes per day, hence the operation use period may be around 540 minutes to around 1,080 minutes. However, the protective cover may be designed to be abrasion resistant for longer or for shorter periods of time. In particular, in some embodiments, a protective cover may be used that is abrasion resistant for much longer than 1,080 minutes, for example, 2,000 minutes, 4,000 minutes, 10,000 minutes or even longer.

In some embodiments, the first magnetic coupling element is at least partly accommodated in a recess or cavity provided in the motion transmitter. In some embodiments, the motion transmitter may comprise a holder element in which the first magnetic coupling element is at least partly accommodated. In some embodiments, the motion transmitter may comprise a rod element, in particular a rod element made from metal such as stainless steel. Such a metal rod is likely to provide a stability not provided by a motion transmitter that is completely made of a plastic material. The rod element may in some embodiments be pivot mounted at the functional element, in particular at a mounting location that is offset from an axis around which the functional element will be driven during operation. Alternatively or additionally, the rod element may be pivot mounted at a holder element, e.g. a holder element as mentioned above that has a recess that at least partly accommodated the first magnetic coupling element. The pivot mounting of the rod element is likely to support relative movement between the rod element and the functional element or the holder element, respectively.

In some embodiments, the attachment section, the protective cover, the first magnetic coupling element and/or the motion transmitter has a centering structure that is intended for at least supporting the centering of the first magnetic coupling element with the second magnetic coupling element during an attachment process.

In some embodiments, the first magnetic coupling element may have at least one indentation or a groove that is filled with plastic material, in particular with injection molded plastic material. For example, the holder element mentioned above may be made in a plastic injection molding step with the first magnetic coupling element being an insert element. Then, a manufacturing step of, for example, snapping the first magnetic coupling element into a holder element can be discarded with and further, the injection molding step may lead to lower clearances or gaps between the first magnetic coupling element and the holder element then in case of a later mounting of these two parts.

In an embodiment, the attachment section is arranged such that the motion transmitter is mounted free of any return force elements that would influence the behavior of a resonant drive provided in the handle section with a further spring. As springs typically have tolerances, a spring in the attachment section that is intended for coupling with a drive shaft of a resonant drive in a handle section could contribute to the spring-mass system that determines the resonance frequency of the resonant drive. Additionally, a spring in the attachment section may also produce additional noise in operation due to the tolerance needed for mounting of the spring. In some embodiments, a handle section for connection, optionally detachable connection with an attachment section as proposed above comprises a second magnetic coupling element arranged at a drive shaft, which second magnetic coupling element may be arranged for establishing a magnetic connection with a first magnetic coupling element provided at the attachment section and a second coupling structure for establishing a connection, in particular a mechanical connection (for example, a force-fit or form-fit connection) with a first coupling structure provided at the attachment section, in particular at the attachment housing. The second magnetic coupling element may comprise at least a permanent magnet or a magnetizable element.

In at least some embodiments, a handle section as proposed may include a linear drive (i.e. a resonant drive providing a linear reciprocal movement or a DC motor having a gear for converting a rotational motion into a oscillatory linear motion) for driving the drive shaft into a linear oscillation in a longitudinal direction (generally parallel to a longitudinal axis of the drive shaft or coinciding with a longitudinal axis of the drive shaft). In some embodiments, the linear drive may provide via the drive shaft a linear oscillatory motion amplitude in a range of between about ±0.1 mm to about ±2.0 mm, in another embodiment, in a range of between about ±0.5 mm to about ±1.5 mm, in another embodiment, in a range of between about ±0.75 mm to about ±1.25 mm, in another embodiment, in a range of between about ±0.9 mm to about ±1.1 mm and in yet another embodiment, a linear oscillatory motion amplitude of about ±1.0 mm. In some embodiments, the attachment section may include a gear assembly that converts the linear motion provided by the drive shaft and transferred to the motion transmitter into a oscillatory rotation having a maximum angular deflection in a range of between about ±5 degrees to about ±40 degrees, in another embodiment, in a range of between about ±10 degrees to ±30 degrees, in another embodiment, in a range of between about ±15 degrees to about ±25 degrees, and in yet another embodiment, about ±20 degrees (where the angular deflection is measured in an unloaded state of the functional element).

The longitudinal axis as referred to in all embodiments generally extends along a longitudinal or lengthwise dimension of the drive shaft or is parallel to a longitudinal axis of the drive shaft or coincides with a longitudinal axis of the drive shaft. The drive shaft means the drive shaft of the motor or extensions of that.

In an embodiment, the second magnetic coupling element may have a protective cover that protects the second magnetic coupling element from corrosion. The protective cover may be abrasion resistant to the extent that during a typical lifetime of the handle section the protective cover stays intact. As an oral hygiene device is used in a wet environment and typically with abrasive and/or corrosive chemicals such as mouth rinses or toothpaste, a thin coating such as for example, a 10 micrometer thick tin coating may be abraded within a rather short period. A protective cover made of an about 20 µm thick or more, optionally about 30 µm or more, further optionally about 40 µm or more, even further optionally about 50 µm or more metal layer, ceramic layer, glass layer or abrasion-resistant plastic or resin layer may be better suitable. In some embodiments, the protective cover may have a thickness of about 60 µm or more, about 70 µm or more, about 80 µm or more, about 90 µm or more, about 100 µm or more, about 150 µm or more or about 200 µm or more and/or any and/or any thickness within or including the values provided above or any ranges including or within the values provided above. The protective cover may be realized as an essentially cup-shaped element that may be mounted by gluing, press-fitting, crimping, shrink-fitting, stamping, welding, snapping or any combination thereof. The protective cover may be in a particular embodiment, a plate or disk that may be glued to the magnetic coupling element. The protective cover for the second magnetic coupling may be configured similarly to the protective cover described heretofore with regard to the first magnetic coupling.

In an embodiment, the second magnetic coupling element may be at least partly accommodated in a recess provided in the drive shaft. In an embodiment, the handle section, the protective cover, the second magnetic coupling element and/or the drive shaft may have a centering structure that is intended for at least supporting the centering of the first magnetic coupling element with the second magnetic coupling element during an attachment process.

In some embodiments, an oral hygiene device may comprise at least an attachment section as proposed and that may further comprise a handle section having a second magnetic coupling element and a second coupling structure for establishing a connection with the first coupling structure provided at the attachment section. In some embodiments, an oral hygiene device may comprise at least an attachment section as proposed and further a handle section in accordance with a handle section as proposed in a previous paragraph above. In some embodiments, the handle section comprises a drive having a drive shaft that is arranged to provide a linear oscillating motion during operation and the contact faces of the magnetic coupling elements are arranged essentially perpendicular to the linear movement direction.

In some embodiments, as will be explained in more detail further below, the magnetic coupling between the first and the second magnetic coupling elements may be designed to at least partially decouple in case of a pull-off force imposed on the magnetic connection that is beyond a threshold force. Such an at least partial decoupling of the magnetic coupling partners is then likely to interrupt the motion transfer and to generate noise, which can be noticed by a user, who is then informed about a too high load.

As an example, in case of the oral hygiene implement being an electric toothbrush and the attachment being a replaceable brush head having as a functional element a bristle carrier mounted for oscillatory rotation, a magnetic coupling between a motor in a handle section of the oral hygiene device and a motion transmitter in the attachment section should be in a coupled state for typical pull-off forces that occur during operation (i.e. brushing of teeth in an example case). Typical pull-off forces that occur during brushing between the first and second magnetic coupling elements may in particular be generated due to friction between treatment elements (for example, bristles) mounted on the carrier and hard or soft tissue in the oral cavity (for example, the teeth or the gums). This friction increases with the pressure force with which the functional element (for example, brush head) is applied onto the hard or soft tissue (for example, the teeth). Typical applied pressure force values may lay in a range of between about 1.5 Newton (N) and about 3.5 N (pressure forces below this range are typically either not used or do not lead to a proper treatment result and pressure values above this range may potentially lead to discomfort and even injuries), in another embodiment in a range of between about 2 N and 3 N. For the above oscillatory rotating brush heads it has been found that the pull-off force that acts at the magnetic coupling may then be above 5 N and in particular above 6 N and in a further embodiment, in a range of between about 6.5 N to about 8.0 N. Higher pull-off forces may then be due to a too high pressure force applied by the user or due to bristles getting stuck in between teeth. In both cases, it may be reasonable that the magnetic coupling is arranged to decouple at a pull-off force above the maximally occurring and allowed pull-off force. Firstly, it may support to indicate to the user that a too high pressure force is applied as the decoupling may be noticeable to the user. Secondly, such decoupling is likely to reduce pain that may occur in case stuck bristles are pulled out of between the teeth when the magnetic coupling would withstand higher pull-off forces. In both cases it is likely that the decoupling leads to an improved protection of hard and soft tissue against abrasion and other kind of damage. Thus, a threshold force may be set to 5 N, 5.5 N, 6 N, 6.5 N, 7 N, 7.5 N, 8 N, 8.5 N, 9 N, 9.5 N, or 10 N, where in particular the threshold force may be set to a value of at least about 6.5 N, in another embodiment, at least about 7 N, in another embodiment at least about 7.5 N and in yet a further embodiment, at least about 8 N. As will be seen further below, the threshold force can in particular be set by designing the magnetic coupling accordingly, for example, by choosing the dimensions of the first and second magnetic coupling elements, choosing the respective materials from which the first and second coupling elements are made, or choosing a gap between the first and second magnetic coupling elements.

While it is here proposed to design the magnetic coupling in a manner that the magnetic coupling decouples in case a pull-off force is applied above a threshold force, the above example was experimentally derived for bristle carriers mounted for driven oscillatory rotation at the attachment housing. While it is not excluded that other functional elements may result in the same threshold force, another threshold force value may be found as preferred based on experimental investigation with other functional elements or for another intended oral hygiene application, for example, tongue cleaning or gum massaging.

In some embodiments, the attachment section has a first magnetic coupling element that comprises a magnetizable element, which may be made from stainless steel so that a further protective cover could be discarded with, which magnetizable element fits into a cylinder of at least about 4.5 mm diameter and of at least about 4.5 mm length. Optionally, the diameter may be at least about 5.0 mm, in another embodiment at least about 5.5 mm. In another embodiment, the length may be at least about 5.5 mm, and in another embodiment at least about 6.5 mm. In some embodiments, the handle section has a second magnetic coupling element that comprises a permanent magnet, which in one example may be made of NdFeB, which permanent magnet fits into a cylinder of at least about 4.5 mm diameter and of at least about 4.5 mm length. Optionally, the diameter may be at least about 5.0 mm, in another embodiment at least about 5.5 mm. In another embodiment, the length may be at least about 5.0 mm, and in another embodiment, at least about 5.5 mm.

In some embodiments, the motion transmitter is non-detachably connected with the attachment section, in particular with a functional element mounted for driven movement.

In the following, a detailed description of several example embodiments will be given. It is noted that all features described in the present disclosure, whether they are disclosed in the previous description of more general embodiments or in the following description of example embodiments, even though they may be described in the context of a particular embodiment, are of course meant to be disclosed as individual features that can be combined with all other disclosed features as long as this would not contradict the gist and scope of the present disclosure. In particular, all features disclosed for either one of the first or second magnetic coupling elements may also be applied to the other one.

FIG. 1 is a perspective depiction of an example embodiment of an oral hygiene device 1, here realized as an electric toothbrush. The oral hygiene device 1 comprises a handle section 200 and an attachment section 100. In one embodiment, the attachment section 100 may be a detachable brush section. The attachment section 100 has a functional element 130, for example, a brush head, which functional element 130 is movably mounted at an attachment housing 150 such that the functional element 130 can be driven into an oscillatory rotation (as shown with double arrow 21) around a rotation axis R that may be perpendicular to the longitudinal axis L of the attachment section 100. Instead of being realized as an electric toothbrush, the oral hygiene device may be realized as an (electric) tongue scraper, an (electric) flossing device, an (electric) interdental cleaner etc. The attachment section may then accordingly be for example, a tongue scraper section, a flossing section, an interdental cleaning section etc. The functional element may be a tongue scraper head, a flossing head, an interdental cleaning head etc.

Figure 2:
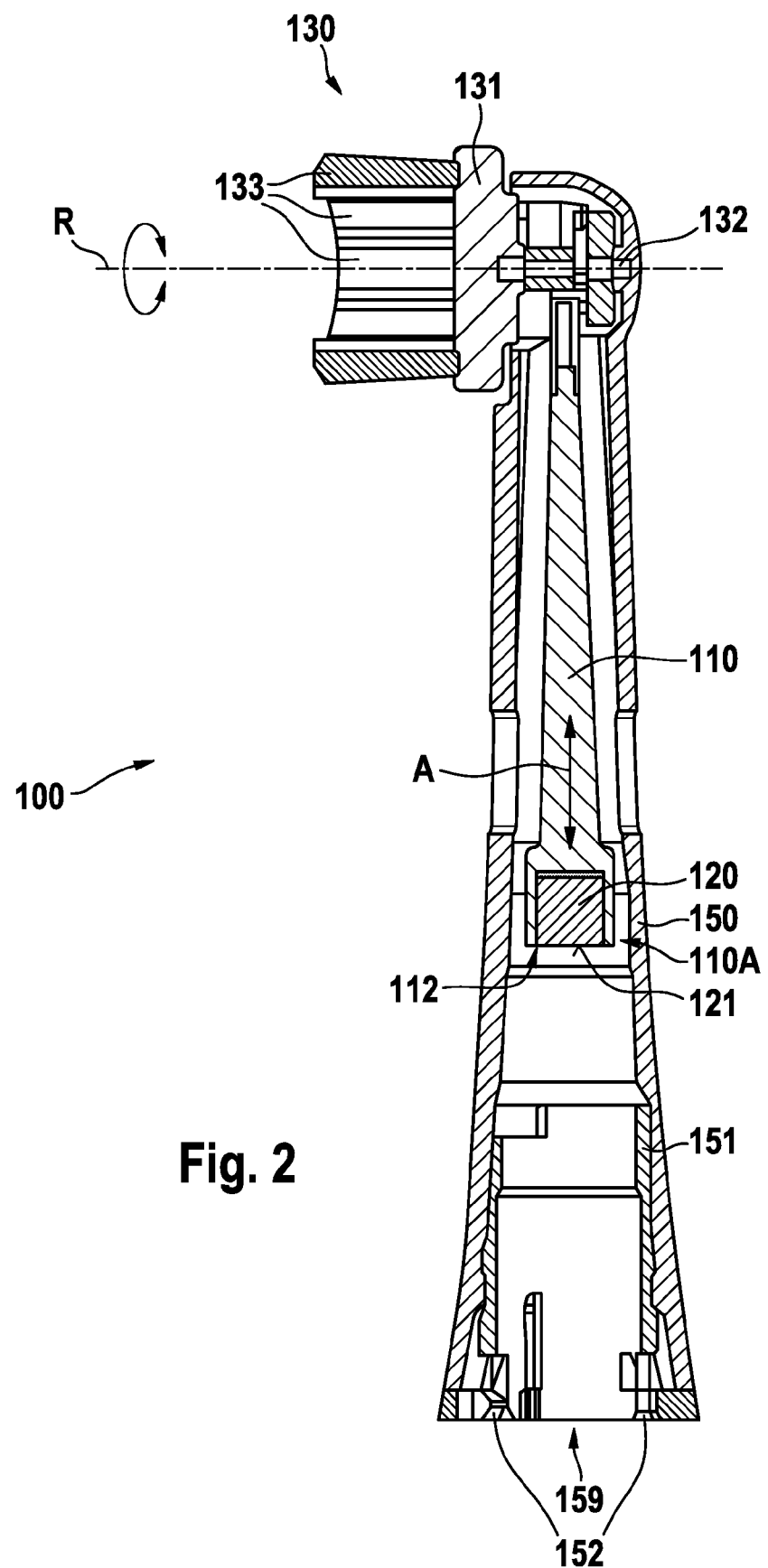
FIG. 2 is a sideways longitudinal cross-sectional cut through an example attachment section.

FIG. 2 is a lateral cross sectional cut through the attachment section 100 taken along a longitudinal axis of the attachment section 100. The attachment section 100 comprises the attachment housing 150 and the functional element 130, which is movably attached to the attachment housing 150.

The functional element 130 may comprise a carrier element 131 on which a plurality of cleaning elements 133 may be mounted for cleaning and massaging parts of the oral cavity such as teeth and gums. The carrier element 131 may be mounted to the attachment housing 150 via a mounting axle 132 for driven oscillatory rotation around a rotation axis R that may be essentially perpendicular to the longitudinal axis (reference numeral L in FIG. 1) of the attachment section 100.

The attachment section 100 may further include a motion transmitter 110 disposed within a cavity 159 formed within the attachment housing 150. The motion transmitter 110 may be functionally connected with the functional element 130 as will be explained in more detail with reference to FIG. 3. Generally and applicable to all embodiments, "functionally connected" shall mean a connection that is not intended to be disconnected and that shall enable that motion transmitted via the motion transmitter is transferred to the functional element. The motion transmitter 110 is arranged for transmission of a linear oscillatory movement to the functional element 130, which linear oscillatory motion may be generally parallel to the longitudinal axis of the attachment section 100 (as indicated by double arrow A). Such a linear oscillatory motion may be provided by a drive shaft of a handle section when the attachment section 100 is in an attached state, as will be explained in more detail with reference to FIG. 5.

In one embodiment, the motion transmitter 110 may include a recess 112 such as a blind hole provided at a first end 110A that is proximal to the opening of the cavity 159, which opening at the end of the attachment section 100 (i.e. the first end 110A of the motion transmitter 110 is distal to the functional element 130). A first magnetic coupling element 120 is disposed in the recess 112. Generally and, as mentioned above for all the described features, applicable for all embodiments, the first magnetic coupling element 120 may be a permanent magnet or a magnetizable element such as a block of magnetizable iron or steel. Typically, austenitic steel is not magnetizable, while martensitic or ferritic steel typically is magnetizable. The first magnetic coupling element 120 has a coupling side 121 that is oriented towards the opening provided at the distal end of the attachment section 100. Generally and applicable to all embodiments, the coupling side 121 may be retracted from the opening at the end of the attachment housing intended for coupling with a handle section so that the magnetic connection is established at a longitudinal position inside of the attachment housing, in particulate where this longitudinal location is retracted by a value lying in the range of between about 0.5 cm to about 5.0 cm, for example, 1.0 cm, 1.5 cm, 2.0 cm, 2.5 cm, 3.0 cm, 3.5 cm, 4.0 cm, 4.5 cm or any other value lying in the mentioned range from the end of the attachment housing and the length of the attachment housing may be in the range of between about 3.0 cm to about 10.0 cm.

The first magnetic coupling element 120 may be secured to the motion transmitter 110 in any suitable manner. For example, the first magnetic coupling element 120 may be glued to the motion transmitter 110, it may be snapped into a recess, it may be secured by injection molding at least a part of the motion transmitter over it or it may be secured by other means as will be explained further below.

In some example embodiments, the first magnetic coupling element is realized as a magnetizable iron or steel element. In case the first magnetic coupling element is realized by a corrosive material such as iron or a NdFeB material (from which relatively strong permanent magnets can be made), at least the coupling side of the first magnetic coupling element may have a protective cover to protect the first magnetic coupling element from corrosion.

In one embodiment, the protective cover may be a coating, a top cover, a cap or a cup, as will be explained in more detail further below. Generally and applicable to all embodiments, any protective cover applied to a first or second magnetic coupling element may lead to a distance between the first and second magnetic coupling elements in the attached state and thus to a reduction in the effective coupling force between the first and second magnetic coupling elements, so that a cover thickness of about or less than 0.5 mm, in another embodiment, about or less than 0.4 mm, in another embodiment, about or less than 0.3 mm, in another embodiment, about or less than 0.2 mm, and in yet another embodiment, about or less than 0.1 mm per cover could be chosen. In other embodiments, the protective cover may comprise a thickness as described previously. In the shown embodiment, the first magnetic coupling element 120 may be glued into the recess. It may have an anti-corrosive coating applied to the coupling side 121 or a protective cover that may be glued over the coupling side 121. In the shown embodiment, it would be sufficient to secure a disc-shaped protective cover onto the coupling side 121 of the first magnetic coupling element 120 as the other sides of the first magnetic coupling element 120 are protected by the surrounding material of the motion transmitter 110.

Generally and applicable to all embodiments, the first magnetic coupling element 120 may be a cylindrical element having its cylinder axis essentially oriented parallel to the longitudinal axis of the attachment section 100, where the diameter of the cylinder may be chosen to be about or larger than 2 mm, in another embodiment about or larger than 3 mm, in yet another embodiment about or larger than 4 mm, in another embodiment about or larger than 5 mm, and in yet another embodiment about or larger than 6 mm, and/or any number or range including or within the values provided.

The cylinder element may have any suitable height. In example embodiments, the height may be chosen to be about or larger than 2 mm, in another embodiment about or larger than 3 mm, in another embodiment about or larger than 4 mm, in another embodiment about or larger than 5 mm, and in yet another embodiment about or larger than 6 mm, and/or any number or range including or within the values provided. In some example embodiments, the height of the first magnetic coupling element may be chosen as large as the diameter. In other embodiments, the second magnetic coupling element may be designed to have any suitable shape. In such a case, the smallest possible cylinder into which such a first magnetic coupling element fits may have a diameter and a height as stated above.

In some example embodiments, the first magnetic coupling 120 is realized as a permanent magnet. In a case in which the attachment section 100 is a disposable attachment section intended for detachable attachment to a handle section 200 of an oral hygiene device, material costs may be considered as one important aspect. Realizing the first magnetic coupling element 120 and the second magnetic coupling element as permanent magnets may lead to a relatively high coupling force, while realizing the first magnetic coupling element 120 as a magnetizable element such as an iron or steel element reduces the material costs of the attachment section 100. The attachment section 100 as shown in FIG. 2 may further comprise an insert element 151 that is snapped into the attachment housing 150 thereby forming part of the attachment housing 150. The insert element 151 may be equipped with a first coupling structure 152 intended for establishing a further coupling (i.e. a coupling different to the magnetic coupling that will be established by the first magnetic coupling element 120) with a handle section of an oral hygiene device in an attached state. In the shown example embodiment, the first coupling structure 152 is realized by mechanical coupling means such as snap hooks or spring elements for clamping projections provided at the handle section. In other example embodiments, the first coupling structure 152 may be realized by a further magnetic coupling element. The longitudinal positions where the magnetic connection is established and where the further connection (e.g. mechanical connection) is established may be separated, in particular by a distance lying in a range of between about 0.5 cm to about 3.0 cm.

Figure 3:
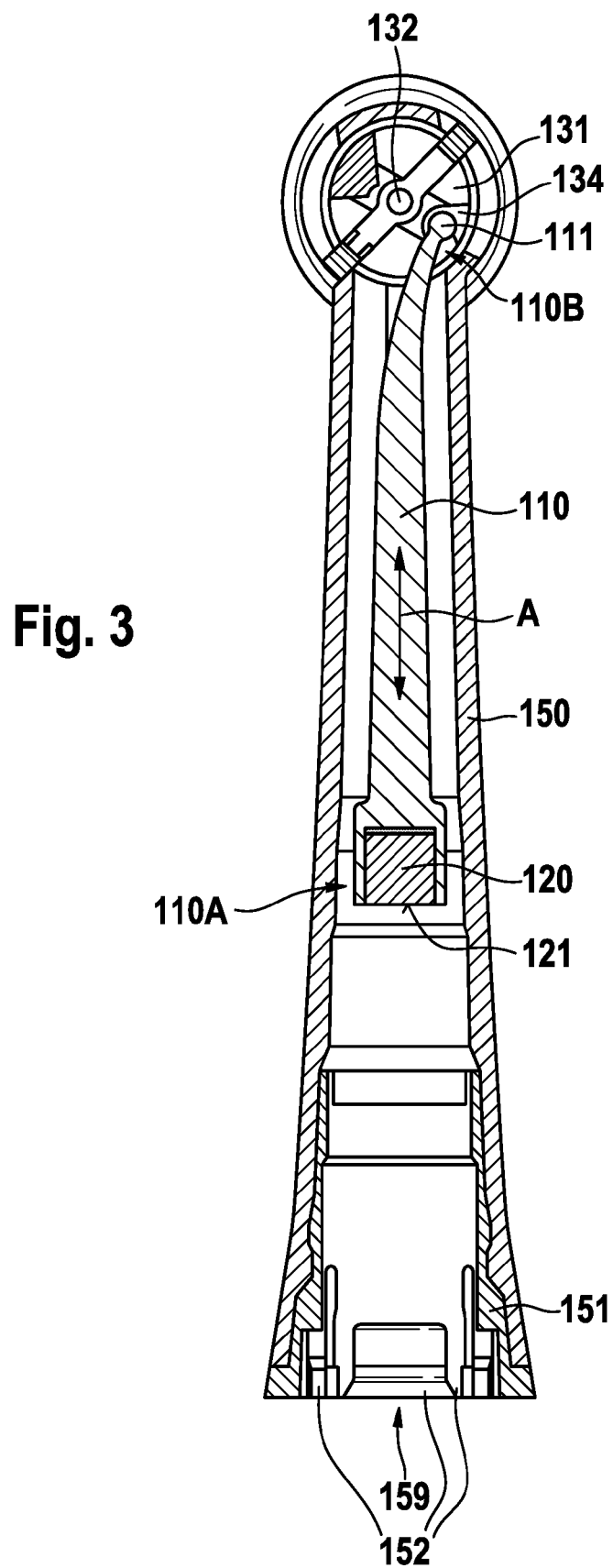
FIG. 3 is a transverse longitudinal cross-sectional cut through the attachment section shown in FIG. 2.

FIG. 3 is a transverse longitudinal cross-sectional cut through the example attachment section shown in FIG. 2, where the viewing direction is towards the cleaning elements. As can be seen from FIG. 3, the motion transmitter 110 is coupled to the functional element by a coupling pin 111 provided at a second end 110B of the motion transmitter 110. The coupling pin 111 establishes a coupling with a coupling section 134 provided at the carrier element 131 at a position that is eccentric with respect to the rotation axis defined by the mounting axle 132. When the motion transmitter 110 is driven into a linear oscillatory movement as indicated by double arrow A, then the carrier element 131 will be driven into an oscillatory rotation around the rotation axis. As will also be explained further below, in some embodiments, the motion transmitter 110 is not associated with any return force element such as a biasing spring that would bias the motion transmitter into a defined rest position whenever the motion transmitter is not being driven.

Figure 4:
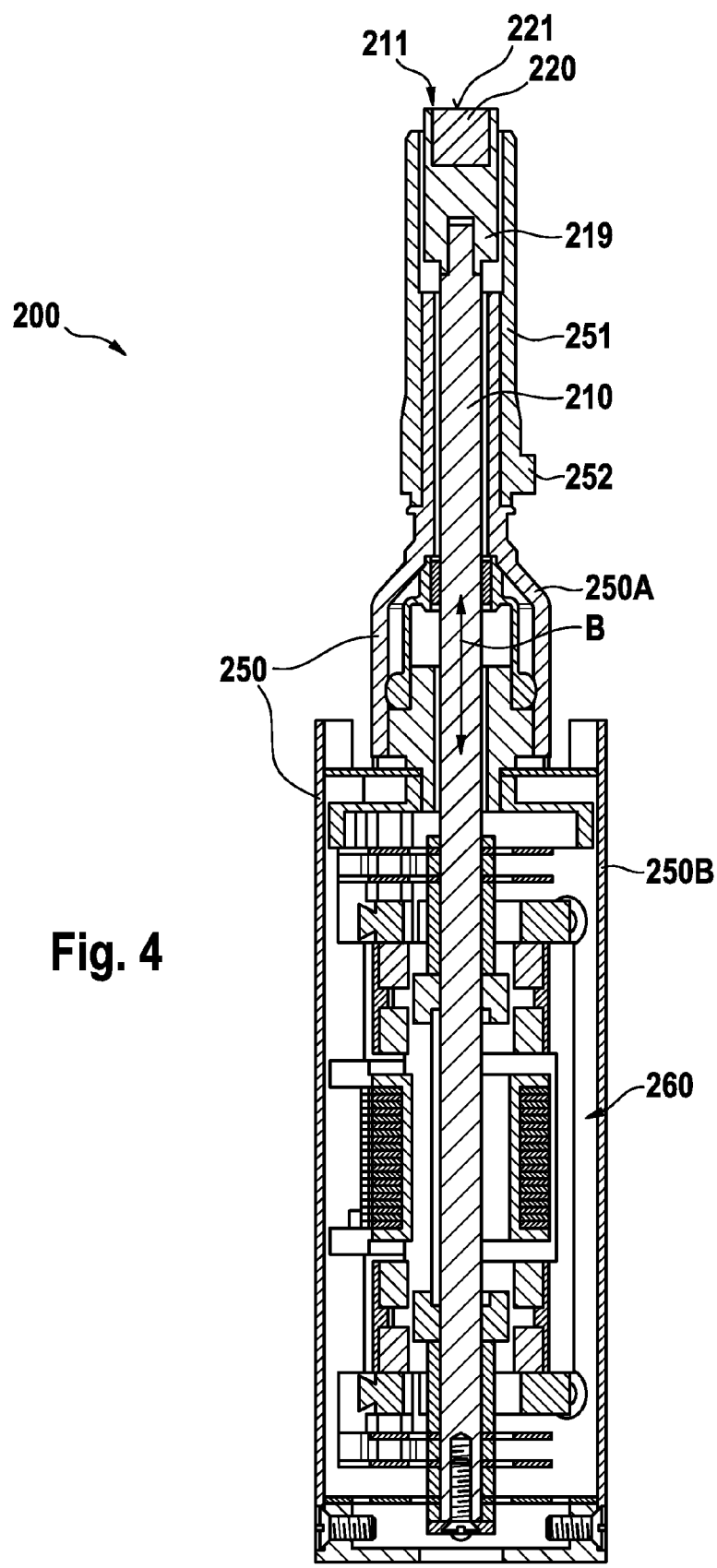
FIG. 4 is a longitudinal cross sectional cut through an example handle section.

FIG. 4 shows a longitudinal cut through a schematic handle section 200. In the shown example embodiment, the handle section 200 comprises a drive shaft 210 that functions as a movable motor part of a resonant linear drive 260, which linear drive 260 is disposed within the handle housing 250. During operation, the linear drive 260 provides for a linear oscillatory movement of the drive shaft 210 as is indicated by double arrow B. In the shown example embodiment, the drive shaft 210 may be prolonged by an extender element 219 that thus forms a part of the drive shaft 210. The extender element 219 can provide an increase in diameter with respect to the diameter of the drive shaft 210. A recess 211 may be provided in the extender element 219 for accommodating a second magnetic coupling element 220. Instead of being accommodated in the extender element 219, the second magnetic coupling element 220 may of course be directly secured at the drive shaft 210 or the drive shaft may be made at least at its tip portion from a permanent magnetic material, which tip would then form the second magnetic coupling element 220. The second magnetic coupling element 220 has a coupling side 221 intended for getting into contact with the respective coupling side 121 (shown in FIG. 2) of the first magnetic coupling element 120 (shown in FIG. 2) of the attachment section when being attached. The coupling side of the first magnetic coupling element and the coupling side of the second magnetic coupling element may be flat or may at least partly be negatives of each other. Generally and applicable to all embodiments, the second magnetic coupling element 220 may be realized as a cylindrical element having its cylinder axis essentially oriented parallel to the longitudinal axis of the drive shaft, where the diameter of the cylinder may be chosen to be about or larger than 2 mm, in another embodiment about or larger than 3 mm, in another embodiment about or larger than 4 mm, in another embodiment about or larger than 5 mm, and in yet another embodiment about or larger than 6 mm or any individual number within or any ranges including or within the values provided. Any suitable height of the cylinder element may be chosen. For example, the height may be chosen to be about or larger than 2 mm, in another embodiment about or larger than 3 mm, in another embodiment about or larger than 4 mm, in another embodiment about or larger than 5 mm, and in yet another embodiment about or larger than 6 mm. In some example embodiments, the height may be chosen as large as the diameter. In other embodiments, the second magnetic coupling element may be designed to have any suitable shape. In such a case, the smallest possible cylinder into which such a second magnetic coupling element fits may have a diameter and a height as stated above.

Generally, the handle section comprises a handle housing at which a second coupling structure intended for establishing a connection with the first coupling structure provided at the attachment section is realized. In the shown example embodiment, the handle section 200 has a handle housing 250 comprising a top handle housing section 250A intended for coupling with the attachment section and a lower handle housing section 250B intended to be gripped by a user's hand. Here, the top handle housing 250A section includes a top part 251 at which a second coupling structure 252 may be realized, The second coupling structure 252 can form a further connection, with the first coupling structure 152 (shown in FIG. 2) of the attachment section. In some embodiments, the second coupling structure 252 and the first coupling structure may establish a coupling which is different than the connection established by the first magnetic coupling and the second magnetic coupling or the coupling may be similar. For example, the coupling established by the first coupling structure and the second coupling structure may include a mechanical lock, magnetic lock, the like, or combinations thereof. In some embodiments having a top housing section 250A and a lower housing section 250B, the top housing section 250A may be arranged for driven motion, for example the top housing section 250A may perform an oscillatory rotation around the longitudinal axis, a longitudinal linear vibration, and/or a linear reciprocation along a direction which is generally parallel to a longitudinal axis of the drive shaft during operation. In such embodiments, the attachment housing that is coupled to the top housing section 250A performs a first motion during operation, for example rotation around the longitudinal axis, longitudinal linear vibration, and/or the linear reciprocation while the motion transmitter may drive the functional element into a second motion. The first and second motions are described further with regard to FIG. 5. In some embodiments, the top housing section 250A is not driven and remains stationary with respect to the lower housing section 250B.

Figure 5:
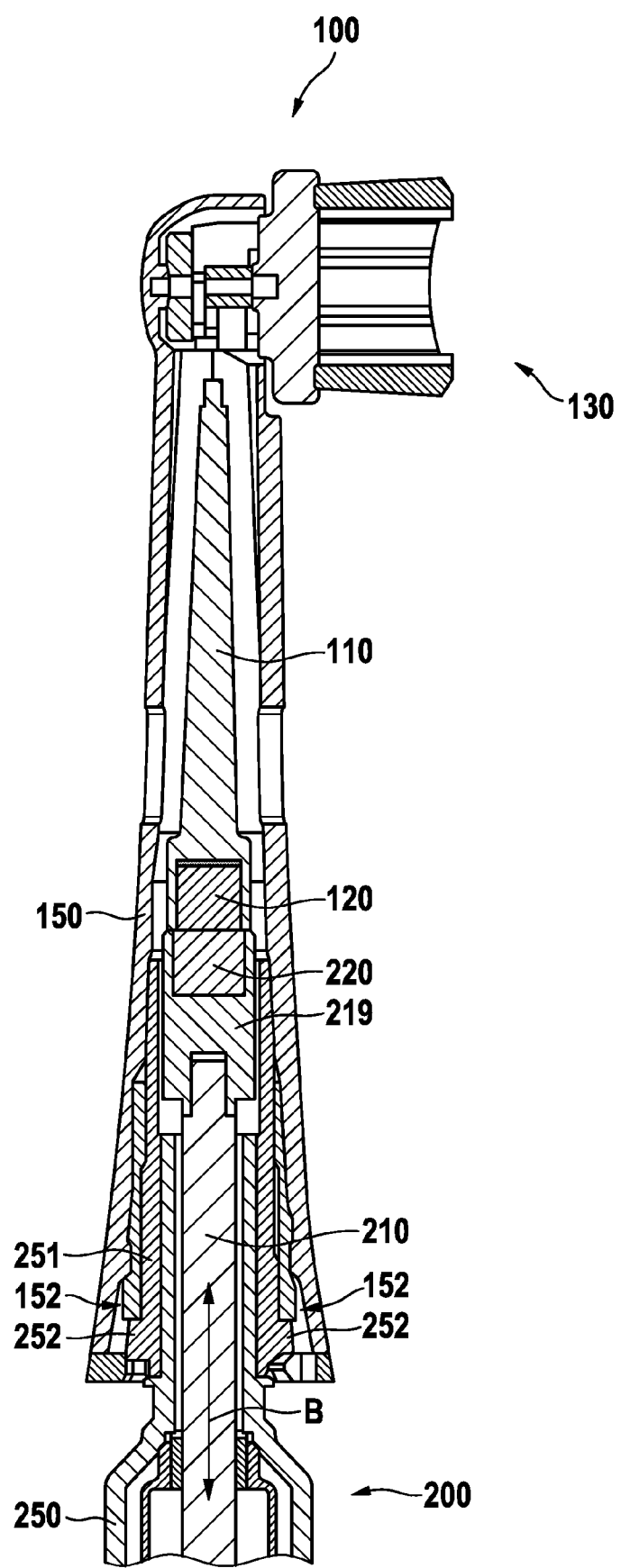
FIG. 5 is a longitudinal cut through a top portion of an example oral hygiene device.

FIG. 5 shows a longitudinal cross sectional cut of an attachment section 100 and a top housing section of a handle section 200 in an attached state. It is shown that the first and second magnetic coupling elements 120 and 220 have established a magnetic connection that couples the drive shaft 210 of the handle section 200 with the motion transmitter 110 of the attachment section 100 such that during operation, a linear reciprocation of the drive shaft 210 as indicated by double arrow B will be transferred to the functional element 130 via the motion transmitter 110. In some embodiments, as the transmitted motion is a linear reciprocation, the magnetic coupling does not need to transmit a rotational movement so that flat coupling sides of the first and second magnetic coupling elements are suitable.

Further, the first and second coupling structures 152 and 252 have established a second connection between the attachment housing 150 and the handle housing 250 such that the attachment section 100 is fixed with respect to the handle housing 250. For those embodiments where the top housing section is driven in an oscillatory rotation around the longitudinal axis, a longitudinal linear vibration, and/or a linear reciprocation along a direction which is generally parallel to a longitudinal axis of the handle 200, the movement of the top housing section is transmitted to the attachment housing via the connection provided between the first and second coupling structures 152 and 252.

As had been said before, the motion transmitter 110 may be mounted free of any return force element. It is known to use a return force element for a motion transmitter provided in an attachment section in case a mechanical connection is to be established between motion transmitter and drive shaft, as then essentially the coupling force needs first to be overcome during the attachment process. Without a return force element, the motion transmitter would potentially be pushed away in the attachment process and the mechanical coupling may not become easily established. For the described magnetic coupling, the first and second magnetic coupling elements will attract each other when the attachment section is attached to the handle section and the motion transmitter will then be moved towards to drive shaft so that the magnetic coupling is established without the need to first overcome any resistance. In particular for a handle section comprising a resonant drive, where the resonant frequency is dependent on the spring-mass system including a return-force element such as a spring acting on the motion transmitter, tolerances in the spring would lead to variations in the resonance frequency of the resonant drive for different attachments. Besides this, discarding a return force element supports a cost efficient manufacture.

Generally and applicable to all embodiments, the first and second magnetic coupling elements 120 and 220 may each be realized as a permanent magnet or a permanent magnet arrangement or as a magnetizable element such as an iron or steel element or an arrangement of such elements. Any kind of permanent magnet material could be used, for example the high energy materials SmCo or NdFeB, either realized as sintered elements or plastic-bonded elements, or any hard ferrite could be utilized such as sintered strontium ferrite. Plastic-bonded permanent magnet elements tend to have a relatively low magnetic flux density when compared with for example sintered permanent magnets. Sintered NdFeB magnets have a relatively high magnetic flux density but are also relatively expensive and are prone to corrosion. Hard ferrite magnets are relatively inexpensive and as ceramic materials less prone to corrosion but have only a limited magnetic flux density. In case that one of the first or second magnetic coupling elements is realized as a magnetizable element, the other one of the first or second magnetic coupling elements is to be realized as a permanent magnet or permanent magnet arrangement. Permanent magnets are widely available e.g. from IBS Magnet, Berlin, Germany.

In some embodiments, at least one of the first or second magnetic coupling elements may be made of or consists at least partially of NdFeB material, in particular of sintered NdFeB material. In some of these embodiments, the second magnetic coupling element provided in the handle section may be made of or consists at least partially of the sintered NdFeB material. The latter allows for realizing the first magnetic coupling element as a relatively cheap magnetizable element such as an iron or steel element or by an arrangement of such elements.

Corrosion-prone permanent magnets like sintered NdFeB magnets may typically be available from a supplier with a thin anti-corrosive coating such as a tin or nickel coating. Unfortunately, toothpaste may abrade these standard coatings rather quickly during operation. Hence, it may then be necessary to equip these permanent magnets with a low-abrasive and anti-corrosive cover to withstand the conditions during operation of an oral hygiene device. Various materials may be chosen for the cover such as low-abrasive plastic materials (for example, for making a deep-drawn plastic cup), ceramics, metal foils, glass etc.

Some permanent magnet materials such as NdFeB have a low operating temperature such as 60 degrees Celsius, which operating temperature is also dependent on the particular dimensions of the permanent magnet. For such permanent magnets, an anti-corrosive protection may not be applied by a plastic injection process during which temperatures of 200 degrees Celsius and more may occur as then the permanent magnet may lose its magnetization. The protective cover may be applied by casting (for example of a resin), gluing (for example of a metal, ceramic, or glass disc), snapping, welding etc. as was already mentioned.

The magnetic coupling established by the first and second coupling elements should withstand a typical pull-off force applied at the functional element as was explained above so that the magnetic coupling is not separated when such a force is applied. In example embodiments, a typical pull-off force applied at the functional element may be up to 10 Newton, i.e. the magnetic coupling should withstand a pull-off force up to a threshold value of about 10 Newton, in another embodiment of up to about 9 Newton, in another embodiment of up to about 8 Newton, in another embodiment of up to about 7 Newton, in yet another embodiment of up to about 6 Newton, in yet another embodiment of up to about 5 Newton, and even in another embodiment of up to about 4 Newton or any value within or including the values provided.

Figure 7:
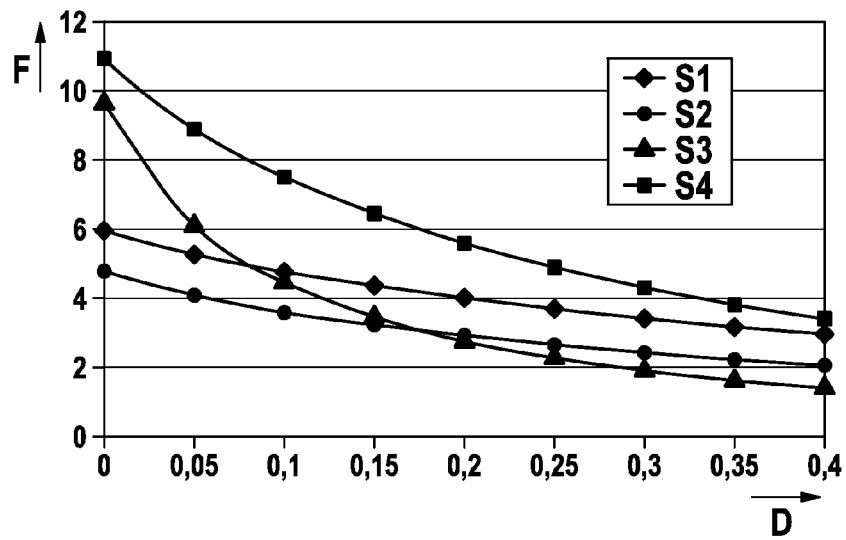
FIG. 7 show simulation results for the force between the coupling partners of the four configurations shown in FIG. 6A-6D.

FIGS. 6A to 6D show four different example configurations S1 to S4 of first and second magnetic coupling elements. FIG. 7 shows simulation results for the effective force that exists between the coupling partners in the coupled state where the results are shown for various values of a gap between the first and second magnetic coupling element, which gap reflects a protective cover on one or both of the magnetic coupling elements.

FIG. 6A shows a first configuration S1 of a first magnetic coupling element 410A being a cylindrical NdFeB permanent magnet and a second magnetic coupling element 420A being a stainless steel cylinder. The diameter d1 of the NdFeB permanent magnet 410A was set to 5 mm in the simulations and the height h1 was set to 5 mm. The diameter d2 of the stainless steel element was set to 5 mm and its height h2 was set to 4.5 mm. An arrow 419A indicates the magnetization direction of the permanent magnet that was here set to be along the longitudinal cylinder axis. The total height of the magnetic coupling arrangement is thus 9.5 mm plus gap thickness.

FIG. 6B shows a second configuration S2, where the only difference to the first configuration S1 shown in FIG. 1 is the magnetization direction 419B of the first magnetic coupling element 410B that is chosen to be perpendicular to the longitudinal cylinder axis.

FIG. 6C shows a third configuration S3 of a first magnetic coupling element 410C and a second magnetic coupling element 420C. The second magnetic coupling element 420C is again assumed to be a stainless steel element, but here having a height of 3.5 mm. The first magnetic coupling element 410C consists of a NdFeB permanent magnet having a height of 5 mm and a diameter of 3.5 mm. The NdFeB permanent magnet is glued into a cup-shaped iron container that has an outer diameter of 5 mm and an inner diameter of 4 mm. The iron container consists of a hollow iron cylinder 4104C and a disc-shaped back iron 4103C. The disc-shaped back iron 4103C has a diameter of 5 mm and a height of 1.5 mm. Overall height of the magnetic coupling arrangement is thus again 9.5 mm plus gap thickness. The magnetization direction of the NdFeB permanent magnet 4101C is indicated by arrow 419C and is assumed to be along the longitudinal cylinder axis.

FIG. 6D shows a fourth configuration S4, where the second magnetic coupling element 420D is as in the third configuration S3 a stainless steel cylinder having a height of 3.5 mm and a diameter of 5 mm. The first magnetic coupling element 410D consists of a first and a second half-cylindrical NdFeB permanent magnet 4101D and 4102D that are oppositely magnetized in longitudinal direction as is indicated by the magnetization arrows 4191D and 4192D, respectively. The cylinder formed by the two half-cylindrical NdFeB permanent magnets has a height of 5 mm and a diameter of 5 mm. On the backside, the two half-cylindrical NdFeB permanent magnets are concluded by a back iron 4103D having a disc-like shape, the disc having a height of 1.5 mm and a diameter of 5 mm. Overall height is again 9.5 mm plus gap thickness. In the simulations that were performed it was assumed that the remanence of the NdFeB permanent magnet material is 1370 mTesla. The properties of stainless steel 1.4021 were calibrated against measurements.

FIG. 7 shows simulation results for the four configurations S1, S2, S3, and S4 described above with reference to FIGS. 6A to 6D. The abscissa indicates the gap between the flat coupling sides of the first and second magnetic coupling elements in millimeters. Gap material was assumed to be air. The ordinate indicates the force between the first and second magnetic coupling elements in the coupled state in Newton. It can be seen that configuration S4 generally leads to the highest threshold force value of the pull-off force that the magnetic coupling can withstand, for example, at 0.1 mm gap configuration S4 leads to a threshold force value of about 7.3 Newton at which the first and second magnetic coupling elements would decouple. The other configurations lead to a coupling force of about 3.4 to 4.9 Newton at a gap of 0.1 mm.

Figure 8:
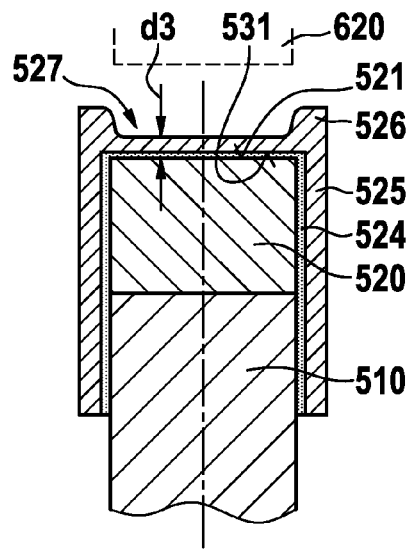
FIG. 8 is a cross sectional cut through a top portion of a drive shaft of an example handle section.

FIG. 8 is a schematic cross sectional cut through the top portion of a drive shaft 510 with a second magnetic coupling element 520. In the embodiment shown, the second magnetic coupling element 520 may be glued into a protection cover 525 having a generally cup-shaped form. The protection cover 525 has a on its top side, where a first magnetic coupling element 620 indicated by a dashed line would approach the second magnetic coupling element 520 during the attachment procedure, a centering structure 526 realized by a raised edge such that a depression 527 is formed into which the first magnetic coupling element 620 fits. The raised edge 526 may be tapered towards the approaching first magnetic coupling element 620 to support the centering function. While the magnetic coupling as such already has a certain self-centering function, a centering structure supports the centering procedure and can avoid misalignments between the first and second magnetic coupling elements. As has been stated before, the first and second magnetic coupling elements could be interchanged with respect to the features described, for example, FIG. 8 may show an example embodiment of a first magnetic coupling element.

Here, the protection cover is realized by a cup that fully accommodates the second magnetic coupling element 520 and that at least partly extends over the drive shaft 510. In such an embodiment, the second magnetic coupling element 520 needs not additionally be secured to the drive shaft 510 as the glue layer 524 fixes the drive shaft 510 and the second magnetic coupling element 520. The thickness d3 of the glue layer 524 and of the protection cover 525 should be chosen as low as possible to avoid reduction of the possible coupling force (see FIG. 7). As a matter of fact, the coupling side 521 does not need to be glued to the protection cover as the side glue layer suffices to establish a fixed connection. The thickness d3 could be chosen to be about or lower than 0.2 mm, in another embodiment to be about or lower than 0.15 mm, in another embodiment to be about or lower than 0.1 mm and even in another embodiment to be about or lower than 0.05 mm or any number within and/or any range within or including the values provided. The material of the protective cover could be a plastic material, a ceramic, a glass, or a (in particular non-magnetizable) metal. In an effort to reduce the thickness of the glue layer 524 and the protective cover, embodiments, are contemplated where the glue layer exists only on the sides of the drive shaft 510 and the second magnetic coupling element 520 but not in between a coupling side 521 of the second magnetic coupling element 520 and a bottom face 531 of the protective cover.

A protective cover made of magnetizable material would in the example shown in FIG. 8 lead to a magnetic short circuit between magnetic north pole and magnetic south pole of the permanent magnet and the achievable force between the magnetic coupling elements would be reduced.

Figure 9:
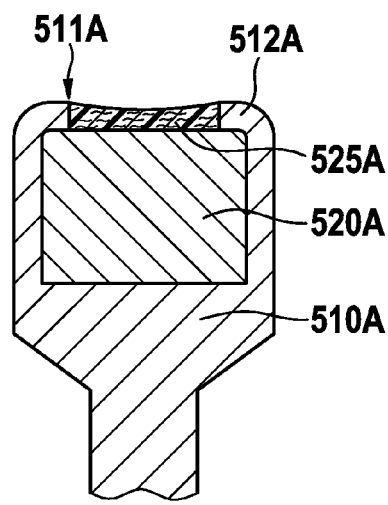
FIG. 9 is a cross sectional cut through a top portion of a drive shaft of an example handle section.

FIG. 9 is a schematic depiction of another embodiment showing the top portion of a drive shaft 510A that has a recess 511A that accommodates a second magnetic coupling element 520A. Bend wall portions 512A fix the second magnetic coupling element in the recess 511A. Prior to introducing the second magnetic coupling element 520A into the recess 511A, the wall portions 512A may have been straight to allow insertion of the second magnetic coupling element 520A into the recess 511A. Then, the wall portions 512A may have been bent, for example, using a forming stamp, such that the second magnetic coupling element 520A is fixed in the recess. A protective cover 525A may cover the remaining opening so that the second magnetic coupling element 520A is protected from corrosion. The protective cover 525A may be a resin or any suitable material as described heretofore. In case that the top portion of the drive shaft 510A is made of a (non-magnetizable) metal or low-abrasive other material that can be formed in the stamping process, the protective layer 525A is effectively protected from being abraded and thus does here not necessarily need to have high abrasion-resistance.

Figure 10:
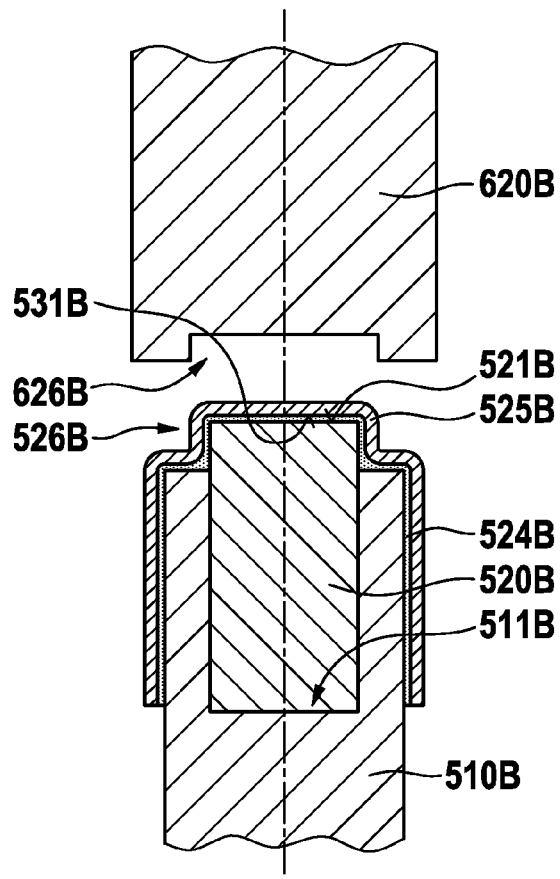
FIG. 10 is a cross sectional cut through a top portion of a drive shaft of a further example handle section.

FIG. 10 is a schematic depiction of another embodiment showing of the top portion of a drive shaft 510B and of a first magnetic coupling element 620B. The drive shaft 510B has a recess 511B that accommodates a second magnetic coupling element 520B, which second magnetic coupling element 520B extends above the drive shaft 510B such that a step-like structure 526B is achieved. A protective cover 525B that may be realized as a deep drawn plastic cup may be glued with a glue layer 524B over the extending top of the second magnetic coupling element 520B and a top part of the drive shaft 510B. The first magnetic coupling element 620B may include a depression 626B that is adapted to the step-like structure 526B so that the step-like structure 526B and the depression 626B cooperate to support the centering of the first and second magnetic coupling elements 620B and 520B in the attachment process. Similar to the embodiment shown in FIG. 8, the glue layer 524B may be absent between a coupling side 521B and a bottom face 531B of the protective cover 525B in an effort to reduce the gap width between the first magnetic coupling element and the second magnetic coupling element. For those embodiments where the first magnetic coupling comprise a protective cap/cover, similar arrangements may be provided.

Figure 11:
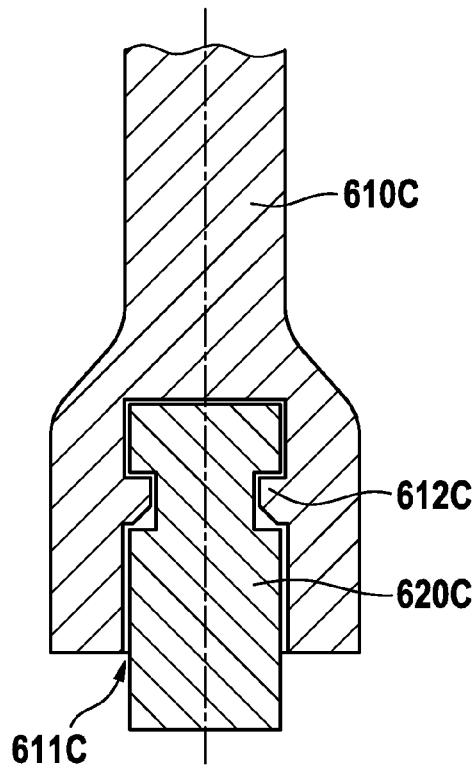
FIG. 11 is a cross sectional cut through a lower portion of a motion transmitter of an example attachment section.

FIG. 11 is a schematic depiction of the lower portion of a motion transmitter 610C in which a recess 611C is provided that accommodates a first magnetic coupling element 620C. The recess 611C may be equipped with snap noses 612C (here realized with a 90 degrees undercut on their backside) so that the first magnetic coupling element 620C that has respective depressions is (non-detachably) secured at the motion transmitter 610C by mechanical means, here realized as snap means. On their frontside (side which is closer to the handle than the backside), the snap noses 612C may be tapered such that the first magnetic coupling element 620C may be pushed into position (snapped) during manufacturing. The motion transmitter may be realized as a plastic part while the first magnetic coupling element 620B may be realized as a non-corrosive steel part.

In other embodiments, the protective cover realized as a cup similar to the shown embodiment could be secured at the drive shaft by for example, crimping, shrink-fitting, welding, or snapping.

Figure 12A:
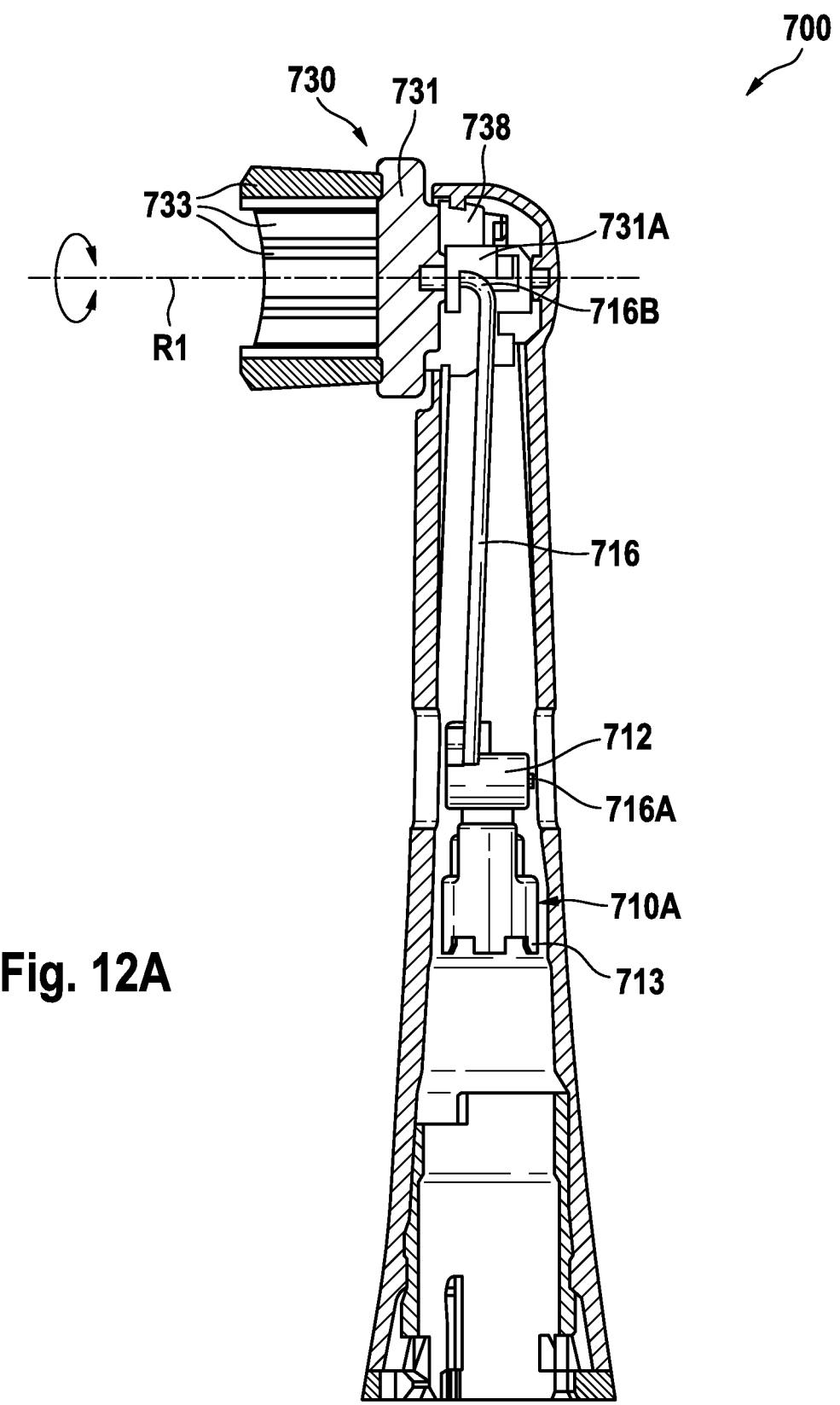
FIG. 12A is a side view depiction of an example embodiment of an attachment section as proposed with the attachment housing being transparent.
Figure 12B:
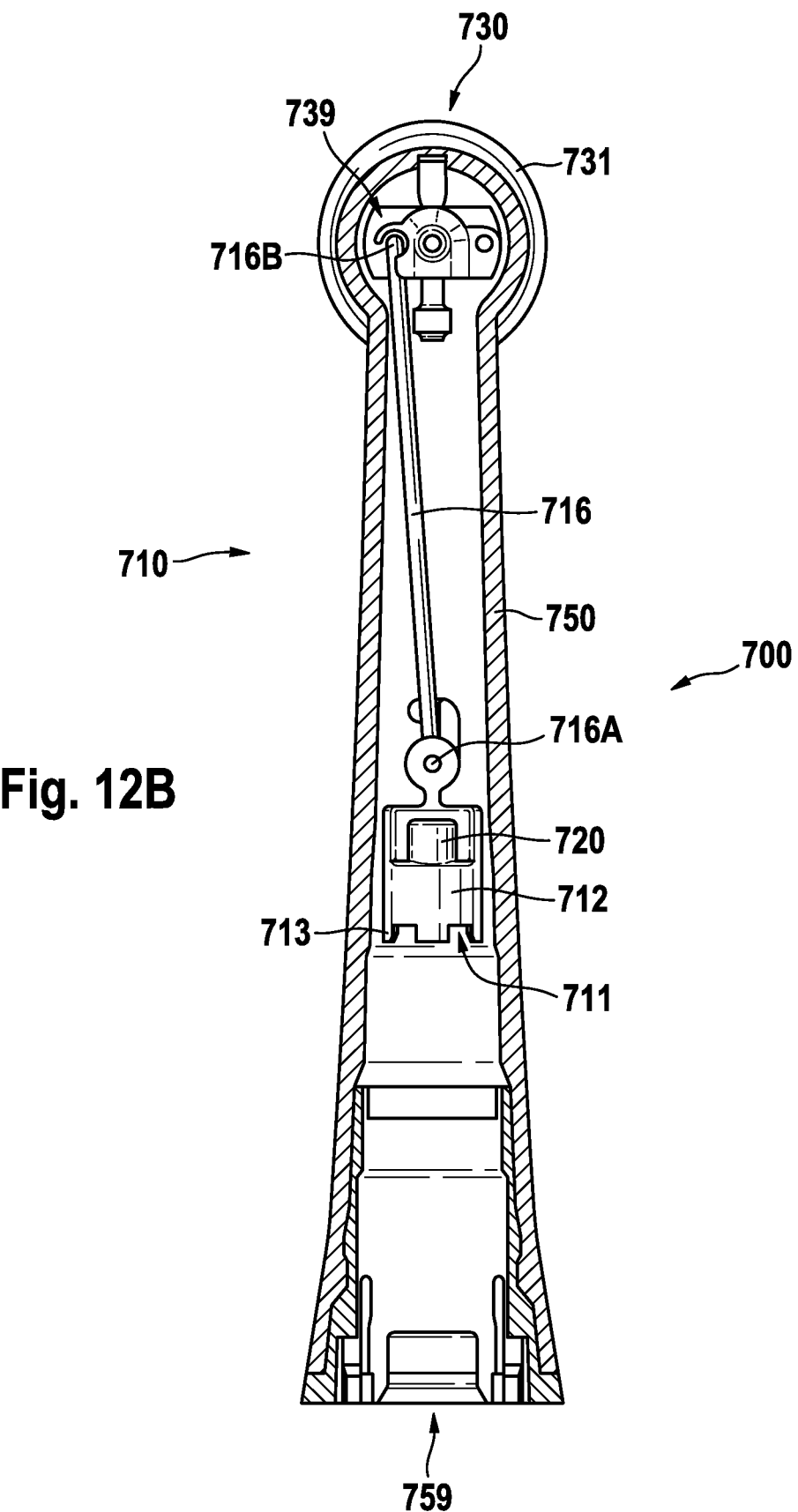
FIG. 12B is a depiction of the embodiment of an attachment section as shown in FIG. 12A, but seen from the backside (the front side being the side where the functional element is mounted)
Figure 12C:
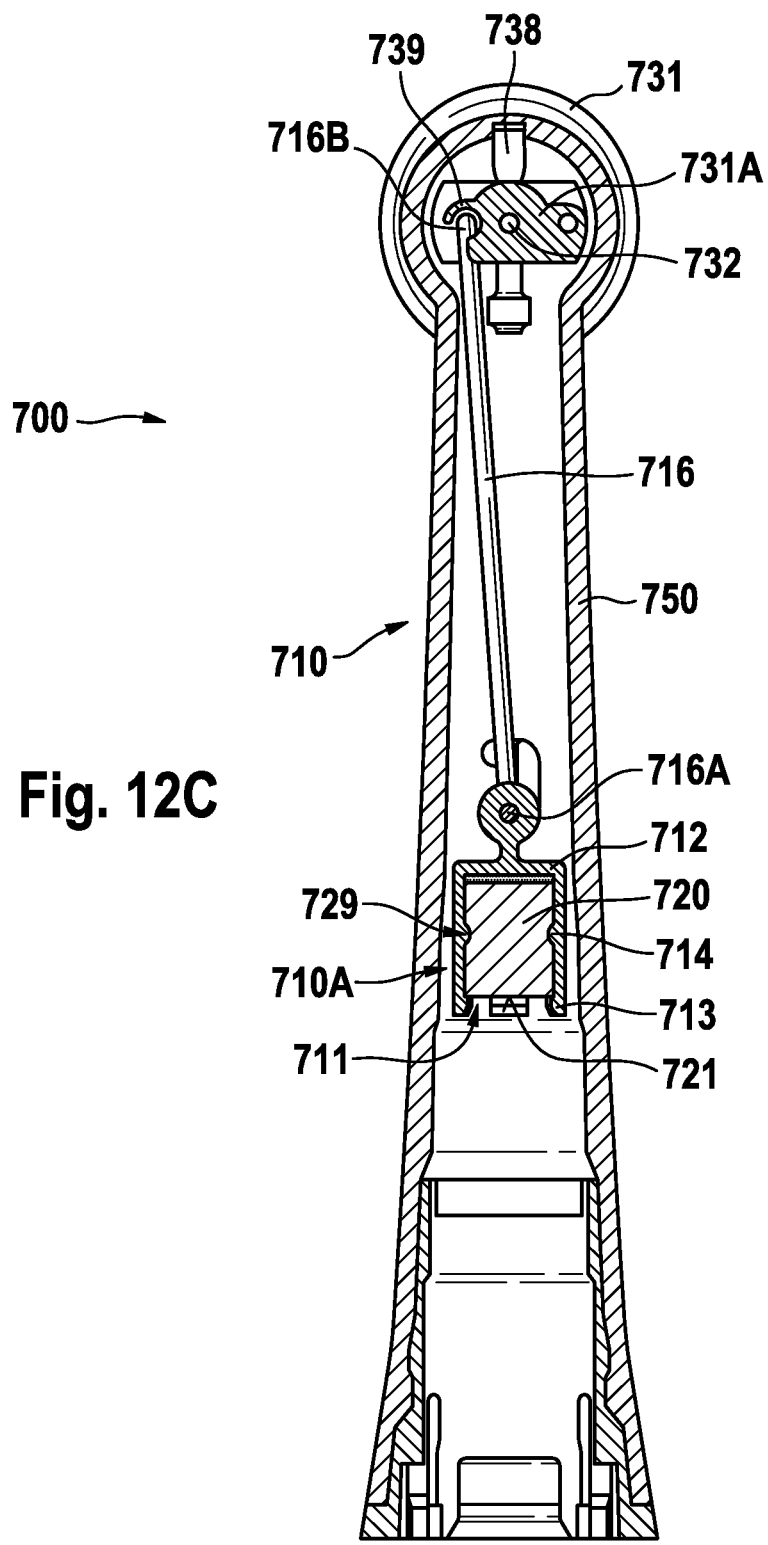
FIG. 12C is a longitudinal cut through the attachment section shown in FIGS. 12A and 12B seen from the backside of the attachment section.

FIGS. 12A, 12B, and 12C show various views of another example embodiment of an attachment section as proposed. Identical parts have the same reference numerals in these three views. Reference is made in the following to all three FIGS. 12A, 12B, and 12C. Not all reference numerals are repeated in all figures.

An attachment section 700 has an attachment housing 750, a functional element 730 realized as a brush head mounted at the attachment housing 750 for driven oscillatory rotation around a rotation axis R1, which rotation axis R1 is essentially perpendicular to a longitudinal extension direction of the attachment section 700. The attachment section 700 further includes a motion transmitter 710 that extends in a cavity 759 formed inside of the attachment housing 750.

The functional element 730 (for example, a brush head) has a carrier element 731 on which cleaning elements such as bristle tufts may be mounted. The carrier element 731 may comprise a coupling element 731A that in particular may be an integral part of the carrier element 731. The carrier element 731 may be mounted at the attachment housing 750 by means of a fixation element 738 so that it cannot be easily detached from the attachment housing 750. The motion transmitter 710 may comprise a holder element 712 and a rod element 716. The holder element 712 may at least partly accommodate a first magnetic coupling element 720 in a recess 711 at a first end 710A of the motion transmitter 710. The rod element 716 may in particular be made from metal such as stainless steel and may optionally be made from a metal wire. A metal rod element may provide a higher rigidity and elasticity than a respective motion transmitter part made of plastic material. A motion transmitter may be made completely as a single integral part from plastic material due to the higher ductility of plastic compared to metal. The rod element 716 may have a first coupling part 716A that is pivot-mounted at the holder element 712 and a second coupling part 716B that is pivot mounted at a coupling section 739 provided at the coupling element 731A of the carrier element 731. At least one of the first or second coupling parts 716A, 716B of the rod element 716 may be a bent rod section that may extend into a bore or blind hole in the holder element 712 or the coupling element 731A, respectively. As can be particularly be seen in FIG. 12C, the first magnetic coupling element 720 may have at least an indentation or groove 729 that is filled with injection molded plastic 714, i.e. the first magnetic coupling element 720 may have been directly overmolded with the holder element 712. This direct overmolding step in the manufacturing leads to minimal gaps or clearances between the first magnetic coupling element 720 and the holder element 712. Generally and applicable to all embodiments, the first magnetic coupling element may be directly overmolded with at least a part of the motion transmitter and a depression present at the first magnetic coupling element may be filled with injection molded plastic material such that the first magnetic coupling element is fixedly secured at this injection molded part of the motion transmitter.

The holder element 712 has protrusions 713 extending in the longitudinal extension direction at the edge of a contact surface 721 of the first magnetic coupling element 720, which protrusions may be tapered radially outwards such that these protrusions form a centering structure that at least supports the centering of the magnetic connection between the first magnetic coupling element 720 and a second magnetic coupling element at a handle section during the attachment of the attachment section 700. The centering functionality also performs in an attached state when the first and second magnetic coupling elements have decoupled due to a too high pull-off force and the high pull-off force has vanished so that the first and second magnetic coupling elements couple again due to the magnetic force acting between them. In particular in cases where one of the first and second magnetic coupling elements is a magnetizable element, a self centering force as between two permanent magnets is not present and an additional centering structure supports to center the two coupling partners and thus to optimize the coupling force.

In some embodiments, cleaning elements arranged on the attachment section may be made from a soft plastic material such as rubber or a thermoplastic elastomer (TPE) or may be made from more rigid plastic material such as polyamide (for example, PA 6.12). Cleaning elements may have any kind of suitable height, which height may be chosen to lie between 0.2 mm (for example, for tongue cleaner structures) and 30 mm, where a typical length of a cleaning element may lie in the range of between about 2.0 mm to about 15.0 mm, in another embodiment between about 5.0 mm and 11.0 mm. Cleaning elements may have any suitable diameter, which diameter may be chosen to lie in a range of between about 0.2 mm to about 20 mm, in another embodiment in a range of between about 0.5 mm to about 8.0 mm.

Additionally, it should be noted that the cleaning elements may comprise any suitable cleaning element and/or may comprise elements which are utilized for massaging gums, cleaning the tongue, providing chemistry to an area of the oral cavity, for example, antimicrobial agents, malodor agents, flavor agents, anti-plaque agents, anti-gingivitis agents, whitening agents, or the like.

For example, in some embodiments, the cleaning elements may comprise tufts. The tufts may comprise a plurality of individual filaments which are securely attached to the head. Such filaments may be polymeric and may include, for example, polyamide or polyester. The longitudinal and cross sectional dimensions of the filaments of the invention and the profile of the filament ends can vary. Additionally, the stiffness, resiliency and shape of the filament end can vary. Some examples of suitable dimensions include a length between about 3 mm to about 15 mm, or any individual number within the range. Additionally, the filaments may include a substantially uniform cross-sectional dimension of between about 100 to about 350 microns, or any individual number within the range. The tips of the filaments may be any suitable shape, examples of which include a smooth tip, a rounded tip, tapered tip, a pointed tip. In some embodiments, the filaments may include a dye which indicates wear of the filaments as described in U.S. Pat. No. 4,802,255. Some examples of suitable filaments for use with the brush are described in U.S. Pat. No. 6,199,242. Other suitable examples of bristles include textured bristles, e.g., single and multicomponent bristles (e.g., bristles formed by coextruding different polymers), crimped bristles, gum massaging bristles, bristles of varying configurations (e.g., bristles having multiple lumens), and/or combinations thereof.

Other suitable examples of cleaning elements include those described in U.S. Patent Application Publication Numbers 2002/0059685; 2005/0000043; 2004/0177462; 2005/0060822; 2004/0154112; U.S. Pat. Nos. 6,151,745; 6,058,541; 6,041,467; 6,553,604; 6,564,416; 6,826,797; 6,993,804; 6,453,497; 6,993,804; 6,041,467; and U.S. patent application Ser. No. 12/008,073, filed on Jan. 8, 2008, now U.S. Pat. No. 8,056,176, entitled, "TOOTHBRUSHES" and 60/928,012, filed on May 7, 2007, entitled "ORAL HYGIENE IMPLEMENTS", all of which are herein incorporated by reference in their entirety. Additionally, any suitable arrangement of cleaning elements may be utilized. Some suitable examples include those described in U.S. Pat. Nos. 5,836,769; 6,564,416; 6,308,367; 6,108,851; 6,058,541; and 5,396,678.

In addition to bristles and/or bristle tufts, the cleaning elements may also include elastomeric structures, foams, combinations thereof, and the like. For example, the cleaning elements may comprise elastomeric fins as described in U.S. Pat. No. 6,553,604 and U.S. Patent Application Publication No. 2007/0251040A1. As yet another example, the cleaning elements may comprise elastomeric cup shaped elements as described in U.S. Patent Publication No. 2004/0154112A1. In some embodiments, the cleaning elements may comprise a combination of elastomeric elements and bristles. As an example, a combination of fins and bristles may be utilized, a combination of an elastomeric cup(s) and bristles may be utilized, and/or combinations of elastomeric elements either alone or in combination with bristles may be utilized. Combinations of elastomeric cleaning elements are described in U.S. Patent Publication No. 2009/0007357A1.

The cleaning elements and/or massaging elements may be attached to the head in any suitable manner. Conventional methods include stapling, anchor free tufting, and injection mold tufting. For those cleaning elements that comprise an elastomer, these elements may be formed integral with one another, e.g. having an integral base portion and extending outward therefrom or discretely. The elastomer elements may be injection molded in the head.

In addition to the cleaning elements described heretofore, the head may comprise a soft tissue cleanser constructed of any suitable material. Some examples of suitable material include elastomeric materials; polypropylene, polyethylene, etc; the like, and/or combinations thereof. The soft tissue cleanser may comprise any suitable soft tissue cleansing elements. Some examples of such elements as well as configurations of soft tissues cleansers on a toothbrush are described in U.S. Patent Application Nos. 2006/0010628; 2005/0166344; 2005/0210612; 2006/0195995; 2008/0189888; 2006/0052806; 2004/0255416; 2005/0000049; 2005/0038461; 2004/0134007; 2006/0026784; 20070049956; 2008/0244849; 2005/0000043; 2007/140959; and U.S. Pat. Nos. 5,980,542; 6,402,768; and 6,102,923.

Additionally, for those embodiments comprise elastomer elements on a first side of the head and a second side of the head, the second side being opposite the first side, the elastomer elements of both sides of the head may be unitarily formed. For example, the head sans the elastomeric elements may comprise openings therethrough which can allow elastomeric material to flow from the first side of the head to the second side of the head.

Materials for manufacturing at least a part such as the housing of the handle section or the housing of the attachment section may be any suitable plastic or non-plastic material, where typical plastic materials may comprise at least one from the group consisting of polypropylene (PP), thermoplastic elastomer (TPE), polyoxymethlylene (POM), a blend of polyester and polycarbonate such as Xylex available from SABIC, Saudi Arabia, acrylonitrile styrene acrylateor (ASA), polybutylene terephthalate (PBT). Instead of plastic, metal, glass, or wood may also be chosen as material for making at least a part of the attachment section.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An attachment section suitable for connection to a handle section of an oral hygiene device, the attachment section comprising:
   an attachment housing having a first coupling structure suitable for establishing a connection with a second coupling structure of the handle section;
   at least a functional element mounted at the attachment housing for driven movement;
   a motion transmitter extending in a cavity formed inside of the attachment housing, the motion transmitter having a first end connected to the functional element and a second end opposite to the first end; and
   a first magnetic coupling element arranged at the second end of the motion transmitter, the first magnetic coupling element including at least a permanent magnet or a magnetizable element suitable for establishing a magnetic connection with a second magnetic coupling element provided in the handle section, and
   wherein the first magnetic coupling element has a protective cover that covers at least a coupling side of the first magnetic coupling element that is intended for establishing the magnetic connection.

2. The attachment section according to claim 1, wherein the motion transmitter is arranged for linear oscillatory motion along a longitudinal direction and the functional element is arranged for an oscillatory motion different to the motion of the motion transmitter.

3. The attachment section according to claim 1, wherein the motion transmitter comprises a rod element.

4. The attachment section according claim 3, wherein the rod element is pivot-mounted at the functional element.

5. The attachment section according to claim 3, wherein the rod element is pivot-mounted at a holder element having a recess at least partly accommodating the first magnetic coupling element.

6. The attachment section according to claim 1, further comprising a centering structure intended for at least supporting the centering of the magnetic connection between the first and second magnetic coupling elements during an attachment process.

7. The attachment section according to claim 1, wherein the motion transmitter is mounted free of any return force elements.

* * * * *